US010122989B2

(12) United States Patent
Fei et al.

(10) Patent No.: US 10,122,989 B2
(45) Date of Patent: Nov. 6, 2018

(54) CUSTOM EARBUD SCANNING AND FABRICATION

(71) Applicant: Lantos Technologies Inc., Woburn, MA (US)

(72) Inventors: Robert J. Fei, Newton, MA (US); Michael L. Rishton, Reading, MA (US); Jonathan Aguilar, Haverhill, MA (US); Lydia Gregoret, Wakefield, MA (US); Keith Guggenberger, Minnetonka, MN (US); Brett Zubiate, Duxbury, MA (US); Brian J. Fligor, Mansfield, MA (US); Xiaowei Chen, Lexington, MA (US); David J. Wilfert, Rockland, MA (US)

(73) Assignee: Lantos Technologies, Inc., Wilmington, MA (US)

( * ) Notice: Subject to any disclaimer, the term of this patent is extended or adjusted under 35 U.S.C. 154(b) by 0 days.

(21) Appl. No.: 15/289,061

(22) Filed: Oct. 7, 2016

(65) Prior Publication Data

US 2017/0104977 A1    Apr. 13, 2017

Related U.S. Application Data

(60) Provisional application No. 62/239,811, filed on Oct. 9, 2015.

(51) Int. Cl.
*H04N 13/00* (2018.01)
*A61B 1/04* (2006.01)
(Continued)

(52) U.S. Cl.
CPC .............. *H04N 13/25* (2018.05); *B33Y 10/00* (2014.12); *B33Y 30/00* (2014.12); *B33Y 50/00* (2014.12);
(Continued)

(58) Field of Classification Search
CPC .............. H04N 13/025; H04N 13/0253; H04N 5/2252; H04N 2005/2255; B33Y 30/00;
(Continued)

(56) References Cited

U.S. PATENT DOCUMENTS

| 3,790,653 A | 2/1974 | Barkey et al. |
| 4,643,733 A | 2/1987 | Becker |

(Continued)

FOREIGN PATENT DOCUMENTS

| CA | 2840602 A1 | 1/2013 |
| JP | H08243262 A | 9/1996 |

(Continued)

OTHER PUBLICATIONS

Park, Annie, "3D scan designs headphones just for you", [retrieved Dec. 19, 2016], http://www.unitedsciences.com/151-2/, Jan. 10, 2015, 2 pages.

(Continued)

*Primary Examiner* — Jared Walker
(74) *Attorney, Agent, or Firm* — GTC Law Group PC & Affiliates

(57) ABSTRACT

A system includes a first scanner having an inflatable membrane configured to be inflated with a medium to conform an exterior surface of the inflatable membrane to an interior shape of a cavity. The medium attenuates, at first rate per unit length, light having a first optical wavelength, and attenuates, at a second rate per unit length, light having a second optical wavelength. An emitter is configured to generate light to illuminate the interior surface and a detector is configured to receive light from the interior surface. The scanner further includes a processor configured to generate a first electronic representation of the interior shape based on the light. A design computer is configured to modify the first electronic representation into a three-dimen- (Continued)

sional shape corresponding to at least a portion of the interior shape and a fabricator configured to fabricate, based at least on the modified first electronic representation, an earbud.

18 Claims, 16 Drawing Sheets

(51) Int. Cl.
| | |
|---|---|
| H04N 13/25 | (2018.01) |
| H04N 13/254 | (2018.01) |
| B33Y 10/00 | (2015.01) |
| B33Y 30/00 | (2015.01) |
| B33Y 50/00 | (2015.01) |
| H04R 1/10 | (2006.01) |
| H04N 5/225 | (2006.01) |

(52) U.S. Cl.
CPC ......... *H04N 13/254* (2018.05); *H04R 1/1058* (2013.01); *H04N 5/2252* (2013.01); *H04N 2005/2255* (2013.01); *H04R 2460/15* (2013.01)

(58) Field of Classification Search
CPC ...... B33Y 50/00; B33Y 10/00; H04R 1/1058; H04R 2460/15
USPC .......................................................... 348/45
See application file for complete search history.

(56) References Cited

U.S. PATENT DOCUMENTS

| | | | |
|---|---|---|---|
| 5,100,587 A | 3/1992 | Clough et al. | |
| 5,504,316 A | 4/1996 | Bridgelall et al. | |
| 8,032,337 B2 | 10/2011 | Deichmann et al. | |
| 8,047,207 B2 | 11/2011 | Perez et al. | |
| 8,107,086 B2 | 1/2012 | Marini et al. | |
| 8,384,916 B2 | 2/2013 | Hart et al. | |
| 8,840,566 B2 | 9/2014 | Seibel et al. | |
| 8,845,526 B2 | 9/2014 | Hart et al. | |
| 9,291,565 B2 | 3/2016 | Hart et al. | |
| 2003/0164952 A1 | 9/2003 | Deichmann et al. | |
| 2005/0191451 A1 | 9/2005 | Osika et al. | |
| 2007/0106012 A1 | 5/2007 | Matyjaszewski et al. | |
| 2008/0027358 A1 | 1/2008 | Gregersen et al. | |
| 2008/0058629 A1 | 3/2008 | Seibel et al. | |
| 2009/0289938 A1 | 11/2009 | Paulsen | |
| 2010/0019170 A1 | 1/2010 | Hart et al. | |
| 2010/0039534 A1 | 2/2010 | Hart et al. | |
| 2010/0042002 A1 | 2/2010 | Hart et al. | |
| 2010/0296664 A1* | 11/2010 | Burgett .................. | A61F 11/08 381/67 |
| 2011/0009702 A1 | 1/2011 | Morishita et al. | |
| 2011/0076608 A1 | 3/2011 | Bergemann et al. | |
| 2011/0290005 A1 | 12/2011 | Hart et al. | |
| 2012/0327426 A1 | 12/2012 | Hart et al. | |
| 2013/0027516 A1 | 1/2013 | Hart et al. | |
| 2013/0078555 A1 | 3/2013 | Orihara et al. | |
| 2013/0261655 A1 | 10/2013 | Drasler et al. | |
| 2014/0272221 A1 | 9/2014 | Forsyth et al. | |
| 2014/0275974 A1 | 9/2014 | Samuels | |
| 2014/0276005 A1 | 9/2014 | Forsyth et al. | |
| 2014/0276105 A1 | 9/2014 | De Brouchoven et al. | |
| 2014/0330133 A1 | 11/2014 | Stern | |
| 2015/0036146 A1 | 2/2015 | Staloff | |
| 2016/0150949 A1 | 6/2016 | Patterson et al. | |
| 2017/0104977 A1 | 4/2017 | Fei et al. | |
| 2018/0178419 A1 | 6/2018 | Fei et al. | |

FOREIGN PATENT DOCUMENTS

| | | |
|---|---|---|
| WO | 2012115863 A2 | 8/2012 |
| WO | 2013003416 A2 | 1/2013 |
| WO | 2014145026 A2 | 9/2014 |
| WO | 2014145058 A1 | 9/2014 |
| WO | 2014145077 A1 | 9/2014 |
| WO | 2015017779 A1 | 2/2015 |
| WO | 2016086005 A1 | 6/2016 |
| WO | 2017062868 A1 | 4/2017 |
| WO | 2017062868 A8 | 4/2017 |
| WO | 2018118772 A9 | 6/2018 |

OTHER PUBLICATIONS

PCT/US16/56132, "International Application Serial No. PCT/US16/56132, International Preliminary Report on Patentability and Written Opinion dated Apr. 19, 2018", Lantos Technologies Inc., 7 Pages.
PCT/US16/56132, "International Application Serial No. PCT/US16/56132, International Search Report and Written Opinion dated Jan. 26, 2017", Lantos Technologies, Inc., 8 pages.
WelchAllyn CompacVideo Otoscope Model 23120 (NTSC) and 23120P (PAL), Operating Instruction Manual, 2000, 16 pages.
"International Search Report and Written Opinion dated Sep. 11, 2014 for PCT application No. PCT/US2014/029662", 6 pages.
"International Search Report and Written Opinion dated Jul. 31, 2014 for PCT application No. PCT/US2014/029712", 6 pages.
"International Search Report and Written Opinion dated Aug. 7, 2014 for PCT application No. PCT/US2014/029738", 6 pages.
PCT/US15/62464, "International Application Serial No. PCT/US15/62464, International Preliminary Report on Patentability, dated May 30, 2017", Lantos Technologies Inc., 5 pages.
PCT/US15/62464, "International Application Serial No. PCT/US15/62464, International Search Report and Written Opinion dated Mar. 31, 2016", Lantos Technologies Inc., 7 pages.
PCT/US17/67010, "International Application Serial No. PCT/US17/67010, International Search Report and the Written Opinion dated Mar. 9, 2018.", Lantos Technologies Inc., 11 pages.
PCT/US2014/029662, "International Application Serial No. PCT/US2014/029662, International Preliminary Report on Patentability dated Sep. 24, 2015", 5 pages.
PCT/US2014/029712, "International Application Serial No. PCT/US2014/029712, International Preliminary Report on Patentability dated Sep. 24, 2015", 5 pages.
PCT/US2014/029738, "International Application Serial No. PCT/US2014/029738 International Preliminary Report on Patentability dated Sep. 24, 2015", 5 pages.

* cited by examiner

CUSTOM EARBUD SCANNING AND FABRICATION

CROSS-REFERENCE TO RELATED APPLICATIONS

The current application is related to/claims priority under 35 U.S.C. § 119(e) to U.S. Provisional Application No. 62/239,811 filed Oct. 9, 2015, the contents of which are hereby incorporated by reference in its entirety.

FIELD

The subject matter described herein relates to producing earbuds and earbud adapters customized to an individual ear.

BACKGROUND

Earbuds must be comfortable and provide a snug fit to provide the best sound quality and reduce ambient noise. To provide a comfortable and snug fit, customized earbuds may be produced that are based the actual shape of an ear. Traditional methods of determining the actual shape of an ear cavity include creating an impression of the ear canal. Creating or taking an impression includes injecting a material into the ear cavity or canal. The material is allowed to harden and conform to the shape of the cavity, and then the material is extracted from the cavity. An impression created this way may cause complications or pain when the impression material is injected into the cavity, when the material is hardening, or when the impression is extracted.

SUMMARY

In one aspect, a first scanner includes an inflatable membrane configured to be inflated with a medium to conform an exterior surface of the inflatable membrane to an interior shape of a cavity. The medium attenuates, at first rate per unit length, light having a first optical wavelength, and attenuates, at a second rate per unit length, light having a second optical wavelength. The scanner also includes an emitter configured to generate light to illuminate the interior surface of the inflatable membrane and a detector configured to receive light from the interior surface of the inflatable membrane. The received light includes light at the first optical wavelength and the second optical wavelength. The scanner further includes a processor configured to generate a first electronic representation of the interior shape based on the received light. The system includes a design computer configured to modify the first electronic representation into a three-dimensional shape corresponding to at least a portion of the interior shape and a fabricator configured to fabricate, based at least on the modified first electronic representation, an earbud.

In some variations, one or more of the following features can optionally be included in any feasible combination.

The first scanner may include a scanning tip. The scanning tip may include the emitter and the detector. The scanning tip may be configured to actuate between an extended position and a retracted position.

The second scanner may include a structured light source and a camera. The second scanner may be configured to generate a second electronic representation of a second shape. The second shape may be of at least one of: a second interior shape of a portion of the cavity and a second portion of a second surface proximate to the cavity. The second scanner may be coupled to the first scanner.

The design computer may be further configured to merge the first electronic representation and the second electronic representation into a combined electronic representation of the interior shape and the second shape. The design computer may execute a computer-aided design application.

The fabricator may include at least one of: a mold for the earbud, the mold based at least on the interior shape, a three-dimensional printer or digital light processing system, and a second apparatus configured to add one or more additional components to the earbud. The one or more additional components may include at least one component for delivering sound to an area proximal to the earbud.

The three-dimensional printer may be configured to fabricate an object comprising a shell with a predetermined thickness, and where the shell corresponds to the interior shape.

A silicone injector may be configured to inject silicone inside of the shell. The silicone may have a hardness between 15 and 75 shore after curing.

In an interrelated aspect, a method includes performing a first scan, with at least a first scanner, of an interior shape of a cavity. The first scan of the interior shape includes inflating an inflatable membrane with a medium. The inflating of the inflatable membrane conforms an exterior surface of the inflatable membrane to the interior shape of the cavity. The first scan also includes generating light from an emitter to at least illuminate the interior surface of the inflatable membrane. The first scan further includes detecting, at a detector, light from the interior surface of the inflatable membrane. The light has a first optical wavelength and a second optical wavelength. The first scan also includes generating, at a processor, a first electronic representation of the interior shape. The generating is based at least on the detected light.

A second scan of a second shape proximate to the cavity is performed. The second scan of the second shape generates a second electronic representation of the second shape.

A design computer modifies the first electronic representation into a three-dimensional shape corresponding to at least a portion of the interior shape. The design computer generates a combined electronic representation including the first electronic representation and the second electronic representation. The fabricator fabricates an earbud. The fabricating is based at least on the combined electronic representation.

In yet another interrelated aspect, a method includes performing a first scan, with at least a first scanner, of an interior shape of a cavity. The first scan of the interior shape includes detecting, at a detector, light comprising a first optical wavelength and a second optical wavelength. The detected light is generated by at least one of: detecting structured light generated from a pattern imprinted on an interior surface of an inflatable membrane and emitting, by the emitter, structured light to form a pattern on the interior surface of the inflatable membrane conforming to an interior shape of an ear and the detected light generated by reflection of the structured light from the interior surface. A processor generates a first electronic representation of the interior shape. The generating is based at least on the detected structured light;

A second scan of a second shape proximate to the cavity is performed. The second scan of the second shape generates a second electronic representation of the second shape. A design computer modifies the first electronic representation into a three-dimensional shape corresponding to at least a portion of the surface. The design computer generates a combined electronic representation including the first electronic representation and the second electronic representation. A fabricator fabricates an earbud. The fabricating is based at least on the combined electronic representation.

In some variations, one or more of the following features can optionally be included in any feasible combination. The second scan may be performed by a second scanner. The second scanner may include at least one of the first scanner, a structured light source and a camera, and a laser rangefinder.

The scanning tip may actuate between an extended position and a retracted position. The actuation may include the emitter and the detector and the scanning tip being actuated during the generation and detection of the light.

A surface may be illuminated with a structured light source, the structured light source emitting light having spatial variations of intensity or wavelength. The illuminated surface may be imaged with a camera, the imaging generating one or more images resulting from the spatially varying light. The second electronic representation of the surface may be generated based at least on the one or more images.

The first electronic representation may be generated based at least on measurements of absorption of the light at the first optical wavelength and measurements of absorption of the light at the second optical wavelength.

The combined electronic representation may correspond to a concha region of an ear and at least a portion of an ear canal.

One or more native references within the first shape and the second shape may be identified based on at least the second electronic representation.

A number of electronic representations may be combined based at least on the one or more native references.

The fabricating may include at least one of: forming, based at least on the interior shape, a mold for the earbud, fabricating the earbud with a three-dimensional printer or a digital light processing system, and adding, with a second apparatus, one or more additional components to the earbud. The one or more the additional components may include at least one component for delivering sound to an area proximal to the earbud.

The fabricating may further include fabricating, with the three-dimensional printer, an object having a shell with a predetermined thickness. The shell may correspond to the interior shape. Silicone may be injected inside of the shell with a silicone injector. The silicone injected inside of the shell may be cured. The shell may be removed to form the earbud.

The above-noted aspects and features may be implemented in systems, apparatus, methods, and/or articles depending on the desired configuration. The details of one or more variations of the subject matter described herein are set forth in the accompanying drawings and the description below. Features and advantages of the subject matter described herein will be apparent from the description and drawings, and from the claims.

Figure 1:
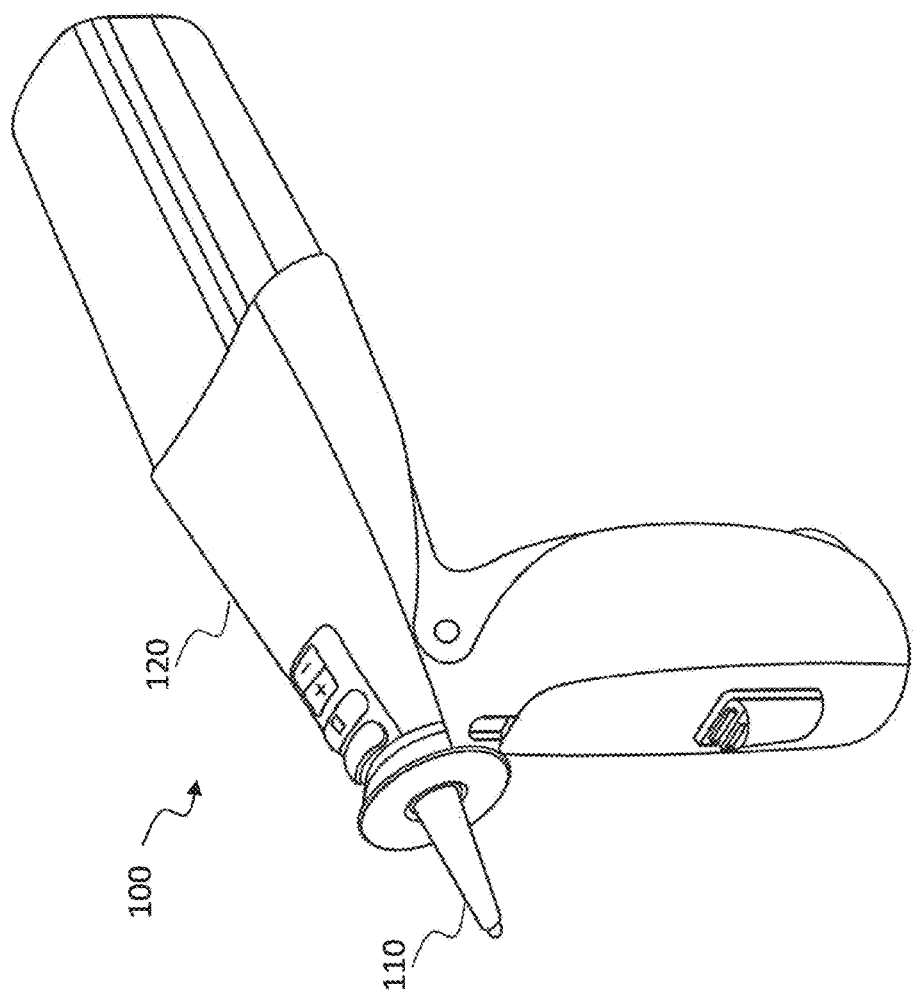
FIG. 1 is a diagram illustrating an example of a system including a three-dimensional (3D) scanner having an inflatable membrane, in accordance with some example embodiments.

Like labels are used to refer to same or similar items in the drawings.

DETAILED DESCRIPTION

An earbud is an object customized to fit the interior shape and exterior shape of a particular person's ear. The earbud may be made of a soft or flexible material in order to be comfortable for the person to wear the earbud in their ear. The earbud may include a speaker or other sound generating device. An earbud adapter may be an object with customized shape to fit the interior or exterior of a particular person's ear. In addition to being customized to fit the ear, it may also customized to fit a commercial earbud or other sound generating device. The commercial earbud may be held into place in the earbud adapter by a clip, latch, or lip of earbud material that holds the commercial earbud in place in the earbud adapter so that the earbud adapter and commercial earbud operate as one object. For example, an earbud adapter may be customized to attach to an earbud and conform to a particular ear. A custom earbud or earbud adapter may provide a more comfortable fit, stay in the ear more securely, provide better sound quality to the person, and/or reduce the ambient noise that passes through or past the earbud.

Some example embodiments, may include a process for generating a custom earbud and/or earbud adapter. The process may include scanning or scoping and measuring the ear canal with an optical scanner. Based on the scan, a mechanical device, such as an earbud, earbud adapter, or earbud shell may be produced from the scan information. An earbud shell (also referred to as a shell) may include a shell made from a thin layer of rigid material formed into the shape of the surface scanned, for example, the ear/ear canal. The earbud shell may serve as a mold in which flexible material is injected and allowed to cure in the shape of the mold and corresponding ear. In some example embodiments, the shell may comprise polyamide and/or urethane. Other materials may be used as well. In some example embodiments, the shell may be produced using a three-dimensional printer to lay down layers of polyamide, urethane, or other material to produce the earbud shell. Although the following disclosure applies to earbuds and earbud adapters, the following may also apply to sleeping plugs and/or noise plugs.

Before providing additional details with respect to exemplary processes for making earbuds or earbud adapters (for example, silicon or rubbery tips or covers that can be coupled to a commercial earbud), the following describes an example of an optical scanner that can be used for scanning the ear.

FIG. 1 is a diagram illustrating an example of a system 100 including a three-dimensional (3D) scanner having an inflatable membrane 110, in accordance with some example embodiments of the current subject matter. The system 100 and accompanying software may generate three-dimensional (3D) scans of a cavity, such as an ear cavity. System 100 may include a 3D scanner 120 including inflatable membrane 110 and a processor, such as a computer. The processor may process scanner data generated by 3D scanner 120 during a scan of the cavity. The processor may form an output, such as a 3D impression of the scanned cavity.

Figure 2:
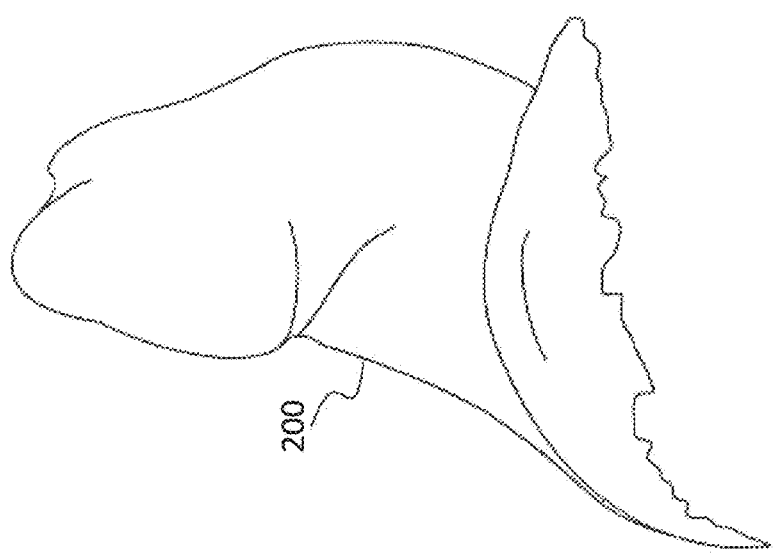
FIG. 2 is a diagram illustrating an example 3D rendering of a cavity formed based on scanner data collected and processed by the 3D scanner, in accordance with some example embodiments.

FIG. 2 is a diagram illustrating an example 3D rendering of a cavity formed based on scanner data collected and processed by the 3D scanner 120, in accordance with some example embodiments. The 3D surface, also referred to herein as an electronic representation 200, may model the scanned cavity, such as an ear cavity, and this 3D surface may be provided to a manufacturer, 3D printer, and the like to form an object. In the case of the ear, the object may be an earpiece or earbud/earbud adapter.

As used herein, the terms "earbud," "earpiece," and "earbud adaptor" can include any sort of appliance that may be worn on the ear, in the ear, or any combination thereof. For example, this may include earbuds for speakers, wireless transmitter/receivers hooked over the ear, earplugs, headphones, personal hearing protection, hearing aids, or the like.

More generally, the terms "earbud," "earpiece," and "earbud adaptor" may also refer to any appliance or object that may be manufactured to conform to any cavity or internal space scanned by any of the scanning techniques described herein. Many of the implementations described herein refer to scanning an ear as part of a process of manufacturing an earbud. However, these implementations do not exclude using any of the apparatus or techniques described herein for the manufacture of other objects, apparatuses, tools, or the like.

Figure 3:
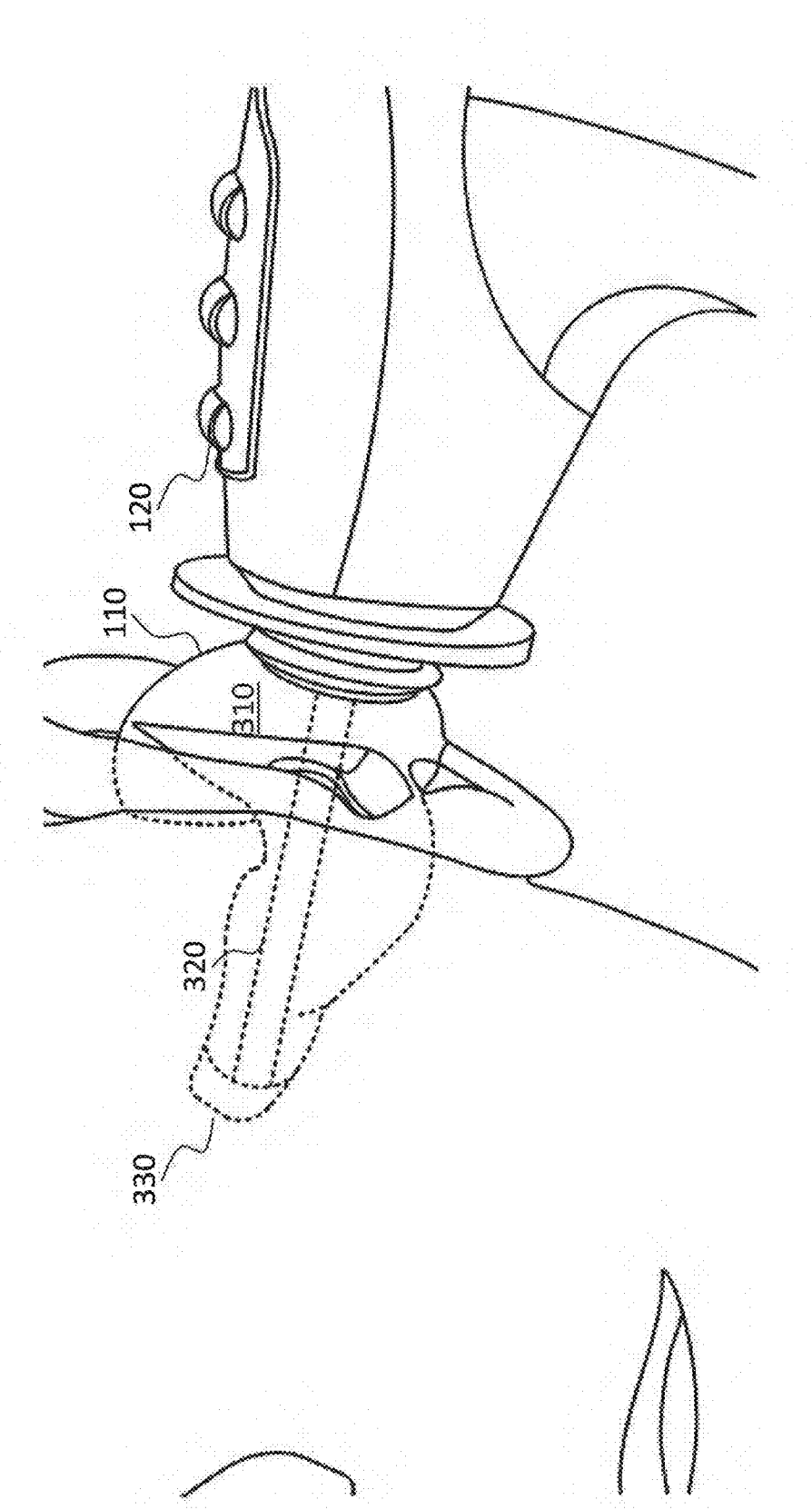
FIG. 3 is a diagram illustrating the 3D scanner with a scanning tip in an extended position, in accordance with some example embodiments.
Figure 4:
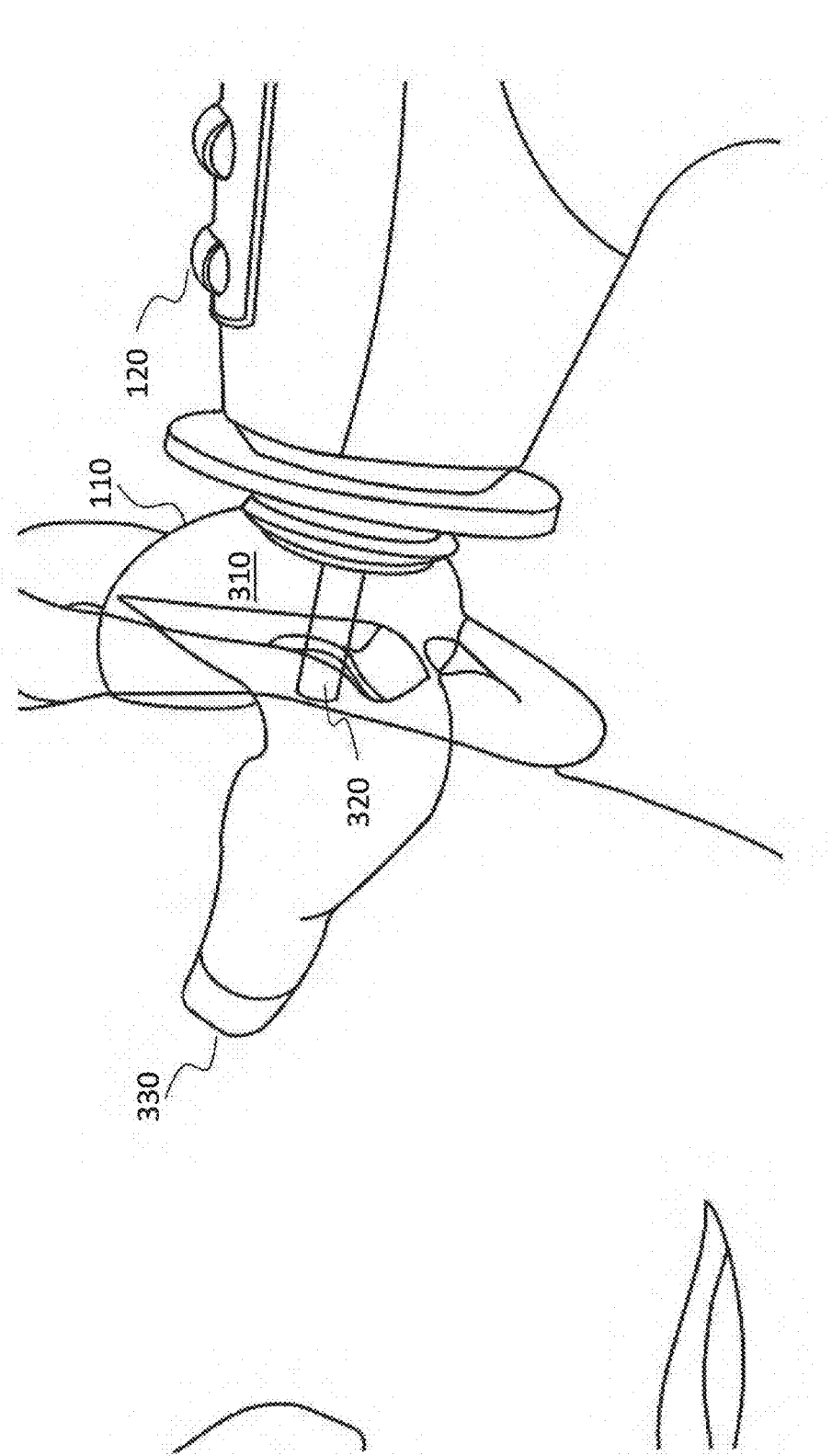
FIG. 4 is a diagram illustrating the 3D scanner with a scanning tip in a retracted position, in accordance with some example embodiments.

FIG. 3 is a diagram illustrating the 3D scanner 120 with a scanning tip 320 in an extended position, in accordance with some example embodiments. FIG. 4 is a diagram illustrating the 3D scanner 120 with a scanning tip 320 in a retracted position, in accordance with some example embodiments. A medium 310 may be used to inflate and expand the interior of the inflatable membrane 110 so that the inflatable membrane 110 conforms an external surface of the inflatable membrane 110 to an interior shape of a cavity 330, or portion of the cavity 330, or any other cavity 330 or surface being scanned.

For example, the medium 310 may be inserted into the inflatable membrane 110, so that inflatable membrane 110 conforms to the cavity 330 being scanned. At this point, scanning tip 320 may scan the interior surface of the inflatable membrane 110 which, when inflated with the medium 310, conforms an external surface of the inflatable membrane 110 to an interior shape of the cavity 330. The interior shape can be, for example, the interior shape of an ear or other object. The scanning tip 320, which may include a light emitter and detector, can actuate between an extended position and a retracted position during the generation and detection of the light used for scanning. In this way, scanning tip 320 may scan the interior surface of the inflatable membrane 110 and thus cavity 330. The scanning tip 320 may generate a 2D image of the inflatable membrane approximating a snap shot of the cavity 330. Each pixel of the 2D image may then be associated with distance information obtained during a scan, for example, the distance from the scanning tip 320 to the scanned portion of the membrane. The combination of the 2D image and distance information for each pixel of the 2D image may correspond to 3D data (for example, a 3D surface representative of the scanned cavity 330). In some implementations, the distance information determined from scanning data can correlate to groups of pixels, instead of a single pixel, on the 2D image.

Medium 310 may, for example, be a liquid, a dissolved gas, a gel, a hydrogel, and/or any combination of the four. The medium 310 may include additives dissolved into, or suspended in, the medium 310 to provide properties. These properties may include, for example, such as selective absorption where one or more wavelengths of light are absorbed more than one or more other wavelengths. To illustrate, medium 310 may include a colored dye, suspension, a luminescent substance, and/or a fluorescent substance (and/or any other material having selective attenuation properties). The medium 310 may also contain a bio-neutralizing, anti-microbial, or anti-oxidizing agent to improve the shelf life of the medium 310 as well as a buffering agent to improve the stability of the medium 310. Moreover, the selective attenuation properties may, as described further below, allow 3D scanner 120 and/or processor to determine the shape of, distance to, and/or other properties of the scanned interior surface of inflatable membrane 110.

The inflatable membrane 110 may be implemented as any viscoelastic, elastic, plastic, and/or any other material that may be inflated to conform to the ear cavity 330, when the inflatable membrane 110 is inserted into the cavity 310 and inflated with medium 310. When the cavity 330 corresponds to an ear canal, inflatable membrane 110 may have an inflated 3D shape and size that is substantially adapted to the ear cavity 330. The inflatable membrane 110 may be used with other cavities and forms, for example, a stomach, an esophagus, a bladder, and or the like. The inflatable membrane 110 may also include, or be coated with, a material to make the membrane fluoresce light of a particular wavelength, or a range of wavelengths, as further described below. In some implementations, the inflatable membrane may have a balloon-like shape with an opening, an interior surface, and an exterior surface. In some implementations, scanning the inflatable membrane 110, rather than the ear cavity 330 directly, may reduce (if not eliminate) the interference caused by artifacts, such as ear hair, wax, and the like, and may thus improve the accuracy of the cavity measurement scan.

Figure 5:
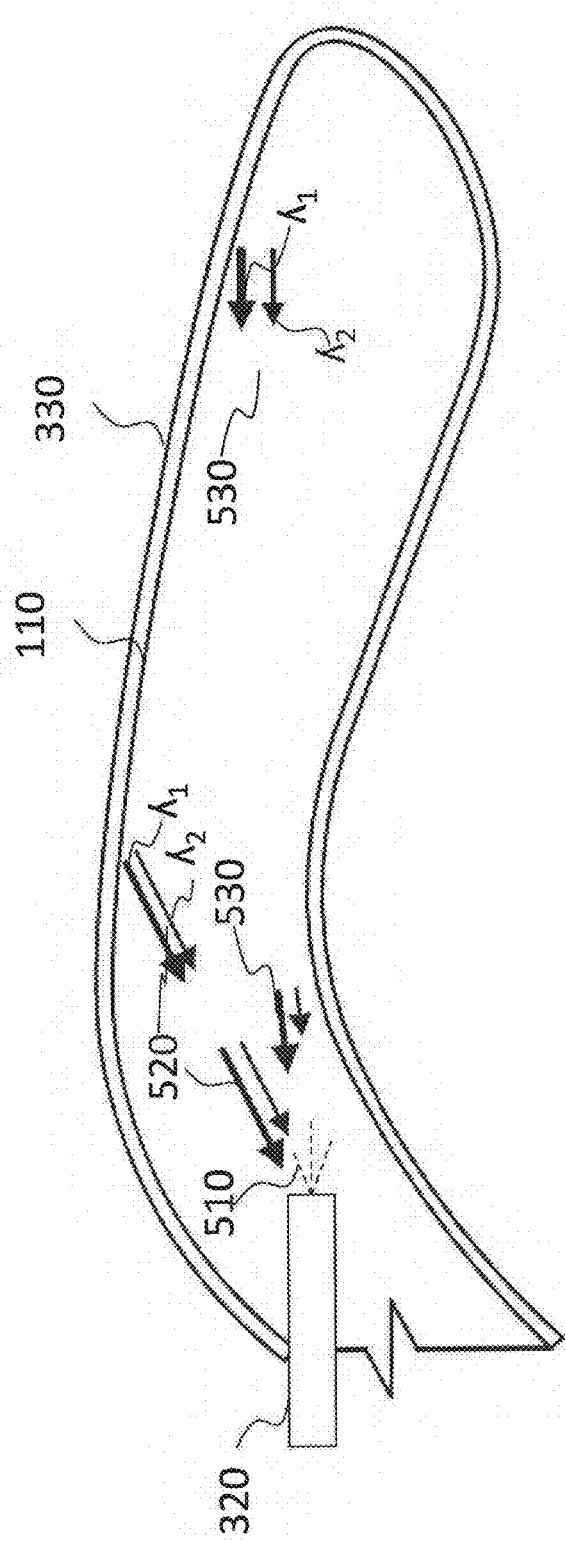
FIG. 5 is a diagram illustrating the attenuation of reflected light by a medium in the inflatable membrane, in accordance with some example embodiments.

FIG. 5 is a diagram illustrating the attenuation of reflected light by a medium 310 in the inflatable membrane 110, in accordance with some example embodiments. The 3D scanner 120 and/or the scanning tip 320 may include at least one light source, such as a light emitting diode, for emitting light into the inflatable membrane 110, which may or may not include medium 310. In FIG. 5, the emitted light 510 is represented by the arrows going out from the scanning tip 320. The scanning tip 320 may also collect and/or detect light 520 and 530 that is emitted from fluorescent material in, or on, the inflatable membrane 110. The light 510 emanating from scanning tip 320 may comprise light used to excite the fluorescent material in, or on, the inflatable membrane 110. Further, light from the fluorescent material in, or on, the inflatable membrane 110 may be referred to as "fluoresced" light, i.e., light resulting from the interaction of the fluorescent material with the light 510 from scanning tip 320.

The inflatable membrane 110 may include a fluorescent material, such as one or more fluorescent dyes, pigments, or other coloring agents. The fluorescent material can be homogenously dispersed within the inflatable membrane 110, although the fluorescent material may be applied in other ways as well (for example, the fluorescent material may be pad printed onto the surface of the inflatable membrane). The fluorescent material may be selected so that the fluorescent material is excited by one or more wavelengths of light 510 emitted by the scanning tip 320. Once the fluorescent material is excited by light 510, the fluorescent material may emit light at two or more wavelengths $\lambda_1$, $\lambda_2$, or a range of wavelengths. For example, wavelength $\lambda_1$ may represent a range of wavelengths associated generally with red, although wavelength $\lambda_1$ may be associated with other parts of the spectrum as well.

In some implementations, the medium 310 may differentially attenuate, for example based on wavelength or other property, light passing through the medium 310. For example, as the two or more wavelengths of light 520 propagate through the medium 310 along paths $l_1$ and $l_2$, $l_1 \neq l_2$, the medium 310 may absorb one or more of the wavelengths of light $\lambda_2$ to a greater degree than one or more other wavelengths of the light. The medium 310 used in the system 100 may also be selected to optimally and preferentially absorb one or more of the wavelengths or a range of wavelengths of light from the fluorescent material of the inflatable membrane. By selecting a medium 310 that complements the fluorescent material, the scan data collected by the 3D scanner 120 may be more accurate.

Similar to the process described with reference to FIG. 3, when the scanning tip 320 of 3D scanner 120 is inserted into ear cavity 330, 3D scanner 120 may pump (or insert in other ways) medium 310 into inflatable membrane 110 until the inflatable membrane 110 conforms to the interior surface of the cavity 330. Once the inflatable membrane 110 is fully inflated, 3D scanner 120 and/or scanning tip 320 may emit light 510 with an emitter, for example a light emitting diode. Light 510 may travel from the scanning tip 320, through medium 310, and excite the fluorescent material on, or in, a portion of the inflatable membrane 110. The light 520, 530 emitted from the fluorescent material on, or in, the inflatable membrane 110 may include at least two wavelengths of light, $\lambda_1$ and $\lambda_2$. One of the wavelengths of light or some ranges of wavelengths of light emitted by the fluorescent material may be differentially attenuated by the medium 310. The differential attenuation may be due to the medium 310 attenuating light at a first optical wavelength $\lambda_1$ at first rate per unit length $\mu_1$, and attenuating light at a second optical wavelength $\lambda_2$ at a second rate per unit length $\mu_2$. The attenuation can be described, for example, as $$I_1(x) = I_1(0)e^{-\mu_1 x} \quad (1)$$

for the attenuation of the intensity of light at wavelength $\lambda_1$ and $$I_2(x) = I_2(0)e^{-\mu_2 x} \quad (2)$$

Here, the initial intensity, for example at the point of emission from the fluorescent material, is $I_1(0)$ or $I_2(0)$. As the light propagates through the medium 310 a distance x along a path between the point of emission and the scanning tip 320, the light may be reduced in intensity or attenuated by the medium 310. The attenuation may be due to, for example, absorption, reflection, scattering, diffraction, or the like.

The light having wavelengths $\lambda_1$, $\lambda_2$ or wavelength ranges of light, may then be received by a detector. The detector may be integrated with the scanning tip 320 and may be configured to receive light from the interior surface of the inflatable membrane 110. The ratio of the intensities of light $\lambda_1$, $\lambda_2$ or the ratio of the integral area of light found under specific ranges may be measured and recorded by 3D scanner 120 and/or processor to determine a distance from the scanning tip 320 to corresponding surface of the membrane 110. For example, the distance x may be determined by inverting Eqns. (1) and (2). The scanning tip 320 may move throughout the interior of inflatable membrane 110 to scan various portions of the interior surface of the inflatable membrane 110. The scanning tip 320 may receive the fluoresced wavelength of light 520, 130 in order to collect data that may be used by the 3D scanner 120 and/or processor to generate an electronic representation 200 of an interior shape of the ear to form a 3D surface representative of the cavity 330. Alternatively, or additionally, the scanning tip 320 may include optical, electronic, or mechanical components for focusing and directing the light used to excite the fluorescent material. Although the scanning tip 320 may include one or more components, such as one or more light emitting diodes, optics, lenses, detectors/CCDs/CMOS sensors, and the like, one or more of these components may be located in other portions of the 3D scanner 120 (for example, an optical fiber may carry light 510 to scanning tip 320).

In some example embodiments, the 3D scanner 120 in accordance with FIGS. 1-5 may scan the deep ear canal. The inflatable membrane may also deform the concha by inflating the inflatable membrane 110 to a predefined pressure or until a predefined deformation of the concha is achieved.

Figure 6:
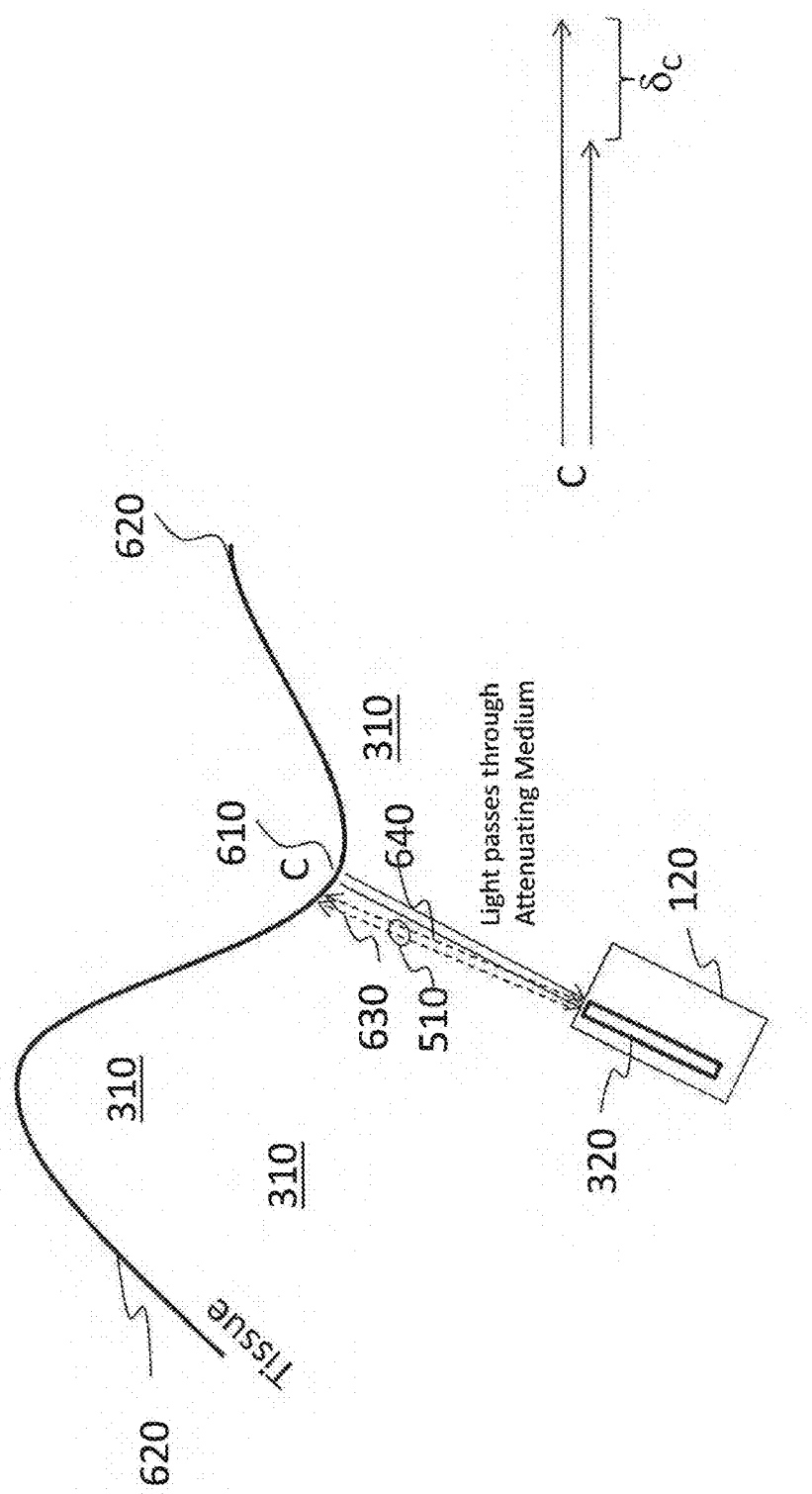
FIG. 6 is a diagram illustrating membrane-less determination of the distance to a proximal location of an inner surface of the ear, in accordance with some example embodiments.
Figure 7:
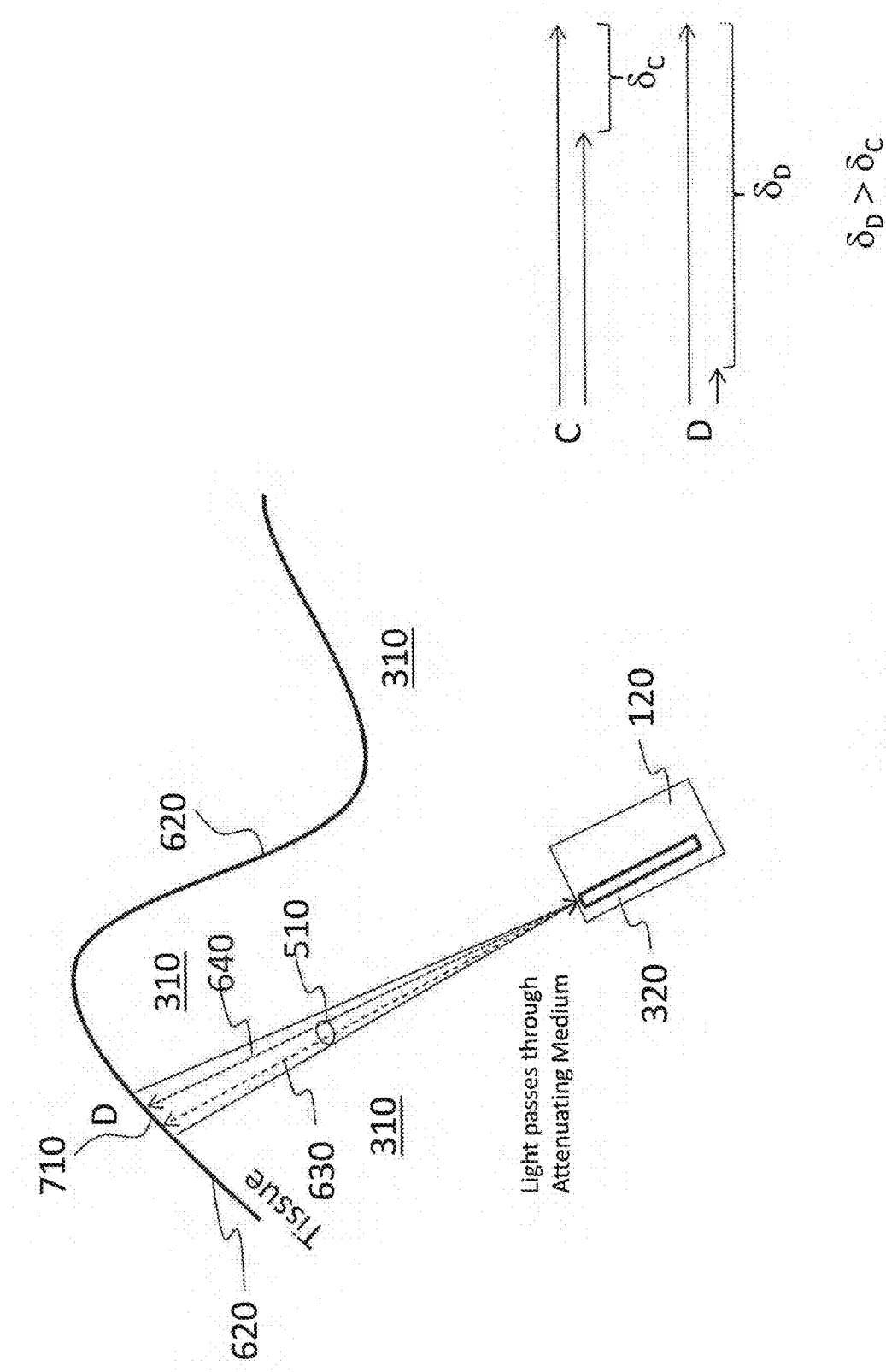
FIG. 7 is a diagram illustrating membrane-less determination of the distance to a distant location of an inner surface of the ear, in accordance with some example embodiments.

FIG. 6 is a diagram illustrating membrane-less determination of the distance to a proximal location 610 of an inner surface 620 of the ear, in accordance with some example embodiments. FIG. 7 is a diagram illustrating membrane-less determination of the distance to a distant location 710 of an inner surface 620 of the ear, in accordance with some example embodiments. The light source may comprise a red LED providing red wavelength light 630, and a green LED providing green wavelength light 640. Any differing wavelength of light may be used. The light source may emit light that reflects from the actual tissue of the interior surface of the ear (i.e. no inflatable membrane 110). Similar to that described above, because the absorbing medium may absorb, for example, red and green light differently, the reflected red and green light from portion C 610 may be received, detected, and represented as a ratio of intensities, such as detected red wavelength intensity over the detected green wavelength intensity. Meanwhile, as shown in FIG. 7 the reflected red and green light from portion D 710 may be received, detected, and represented as a ratio of intensities as well. Given that the distance from portion D 710 to the distal portion of the scanning tip 320 (where the light receiver is located) is greater than the corresponding distance between portion C 610 and receiver, the medium 310 has a greater attenuating effect on the reflected light from portion D 710 as shown by the inset graphs. However, secondary reflections may be a source of noise for the measurement. In some embodiments, the selection of wavelengths used can reduce this noise.

Figure 8:
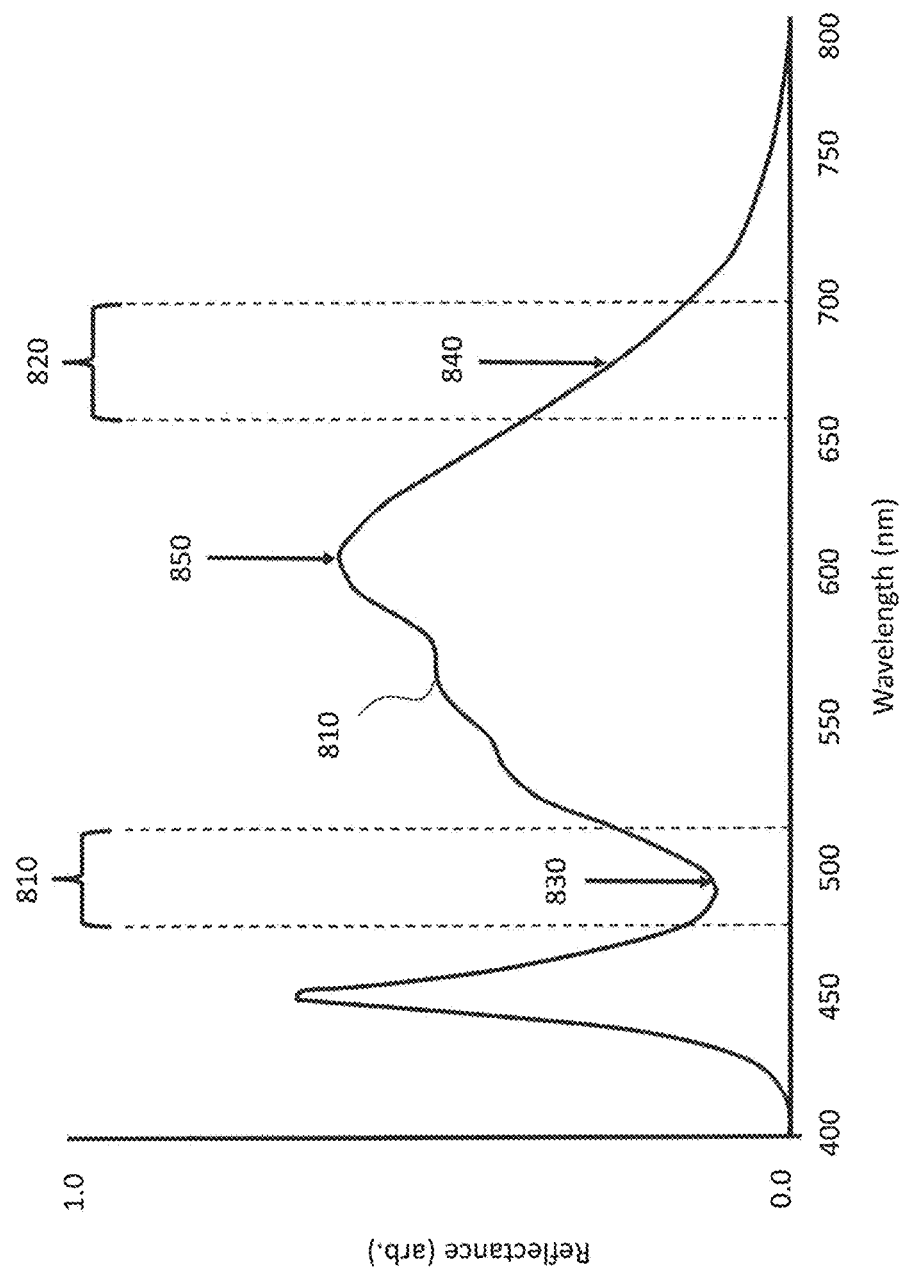
FIG. 8 is a diagram illustrating an exemplary reflectance spectra of a portion of an ear, in accordance with some example embodiments.

FIG. 8 is a diagram illustrating an exemplary reflectance spectra 810 of a portion of an ear, in accordance with some example embodiments. In some embodiments, selection of the two different wavelengths of light may be chosen such that their reflectance from the interior surface of the ear is low. For example, when the reflectance of the tissue is low, then each subsequent reflection reduces the intensity by a factor of 1/R, where R is the reflectance. Combined with the absorbing properties of the medium 310, this preferentially attenuate the light received at the detector that was not due to the primary reflection from the point whose distance from the detector is being determined. FIG. 8 shows, for example, that the a first wavelength may be selected, for example corresponding to green light within band 820 and a second wavelength may be selected, for example corresponding to red within band 830, so that these bands 810 and 820 are located where the reflectance due to the tissue on the surface of the cavity 330 is at a first minima 830 or at a reduced reflectance 840 relative to another portion of the spectra. In the example of FIG. 8, the reflectance from the tissue on the surface of the cavity 330 also contains a maxima 850, so the reflectance from the tissue at this wavelength may contribute to noise or interference at the detector. In some example embodiments, the scanning tip 320 may include a green light source in the range of 475-505 nanometers and a red light source in the range of 655-700 nanometers.

Although some of the examples described herein refer to using two wavelengths at red and green, other wavelengths may be used as well. For example, the intensity of other wavelengths of light can be detected at the scanning tip 320 and then measured and compared may include an combination of the following: violet light (approximately 380 to 450 nm), blue light (approximately 450 to 495 nm), green light (approximately 495 to 570 nm), yellow light (approximately 570 to 590 nm), orange light (approximately 590 to 620 nm), and/or red light (620-750 nm).

Figure 9:
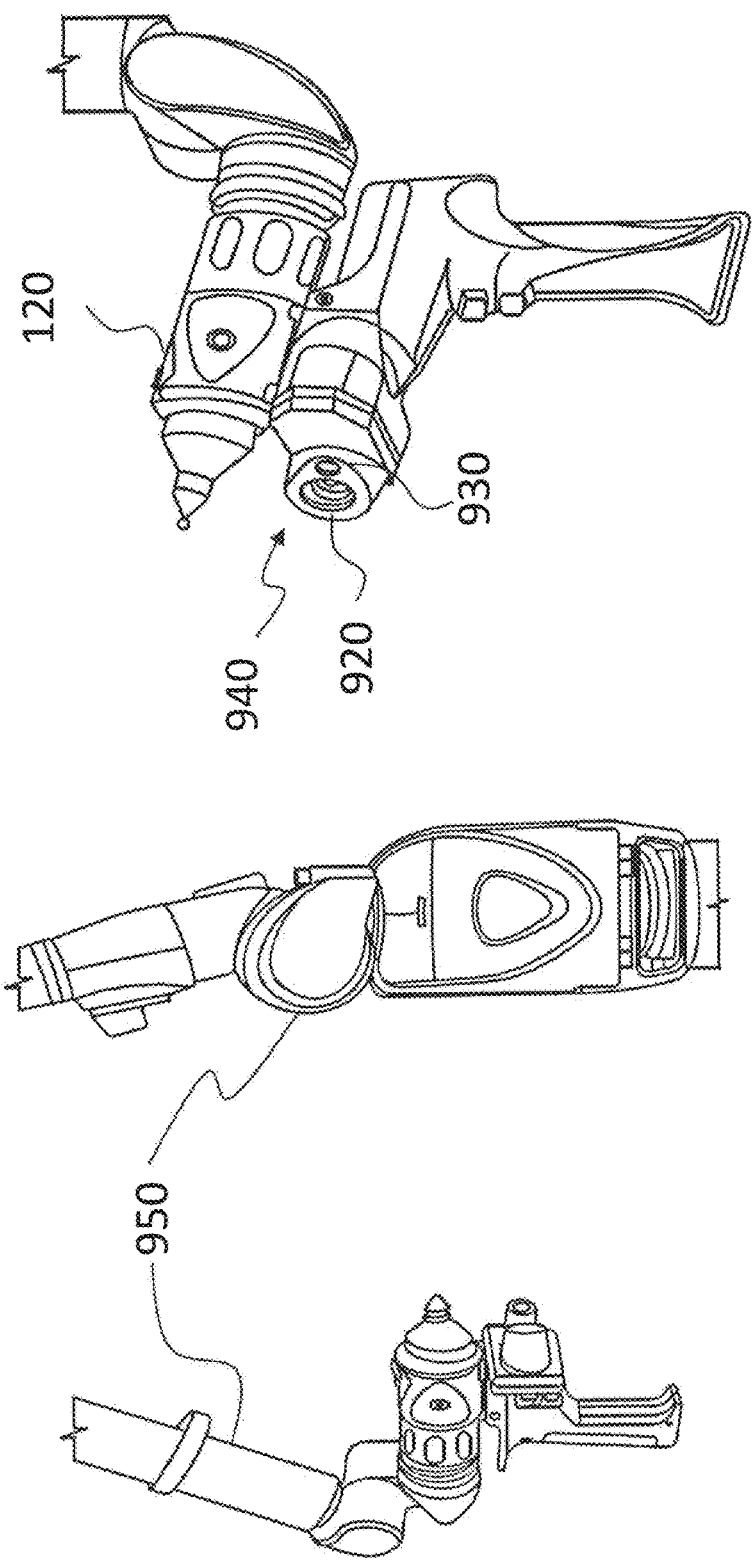
FIG. 9 is a diagram illustrating a serial linkage between a structured light source and camera, in accordance with some example embodiments.

FIG. 9 is a diagram illustrating a serial linkage between a structured light source 910 and camera 920, in accordance with some example embodiments. When making multiple scans with the same scanner or different types of scanners, the scanners can be rigidly coupled, made integral, or otherwise mechanically joined so that the relative position of each scanner is known when combining the resultant scan images.

The 3D scanner 120 such as the scanner disclosed in FIGS. 1-5 may be used to scan the deep ear canal. A structured light source/camera assembly 940 integrating the structured light source 910 and camera 920 is also depicted in FIG. 9. A mechanical linkage between the structured light source/camera assembly 940 and the 3D scanner 120 may provide more accurate position information for the scan data. For example, a serial linkage may be used between the structured light source/camera assembly 940 and the 3D scanner 120. The serial linkage may include mechanically coupling the 3D scanner 120 to the structured light source/camera assembly 940 where both may also mechanically coupled to a robotic arm 950 or other gantry. The robotic arm 950 may be configured to monitor the position and orientation of the coupled 3D scanner 120 and structured light source/camera assembly 161. For example, the 3D scanner 120 may be used to scan a portion of the ear. Then, the structured light source/camera assembly 940 may be translated by the arm into position to scan the same (or different) portion of the ear. Combining the data on the positions of each type of scanner when the scan was made may allow the spatial data or generated 3D surfaces for the two scans to be synchronized for combination to form a composite scan.

In some example embodiments, the concha region may be scanned using a structured light source 920 and a camera 910 without deforming the concha. Methods described herein that do not rely on physical contact between the scanning implement and the surface being scanned can avoid the creation of artifact or other distortions in the measurements of the scanned surface. In some example embodiments, a scan of the ear canal including the deep ear canal and the concha may include two scans; one with the 3D scanner 120 and another scan performed using structured light and/or direct imaging by a camera. The two scans can be aligned and merged using common locations at or near the aperture of the ear canal and interpolate/smooth the transition between the two surfaces in the scans. For example, the two scans may be merged by a design computer to produce a combined scan or model of two or more scanned surfaces or shapes. In some implementations, the camera 920, detector, or other imaging receiver may include a stereoscopic camera or optical system. A stereoscopic camera may enable 3D images to be acquired without having to use structured light or an inflatable membrane 110. However, some implementations can combine the stereoscopic camera with any of the other imaging techniques described herein.

Figure 10:
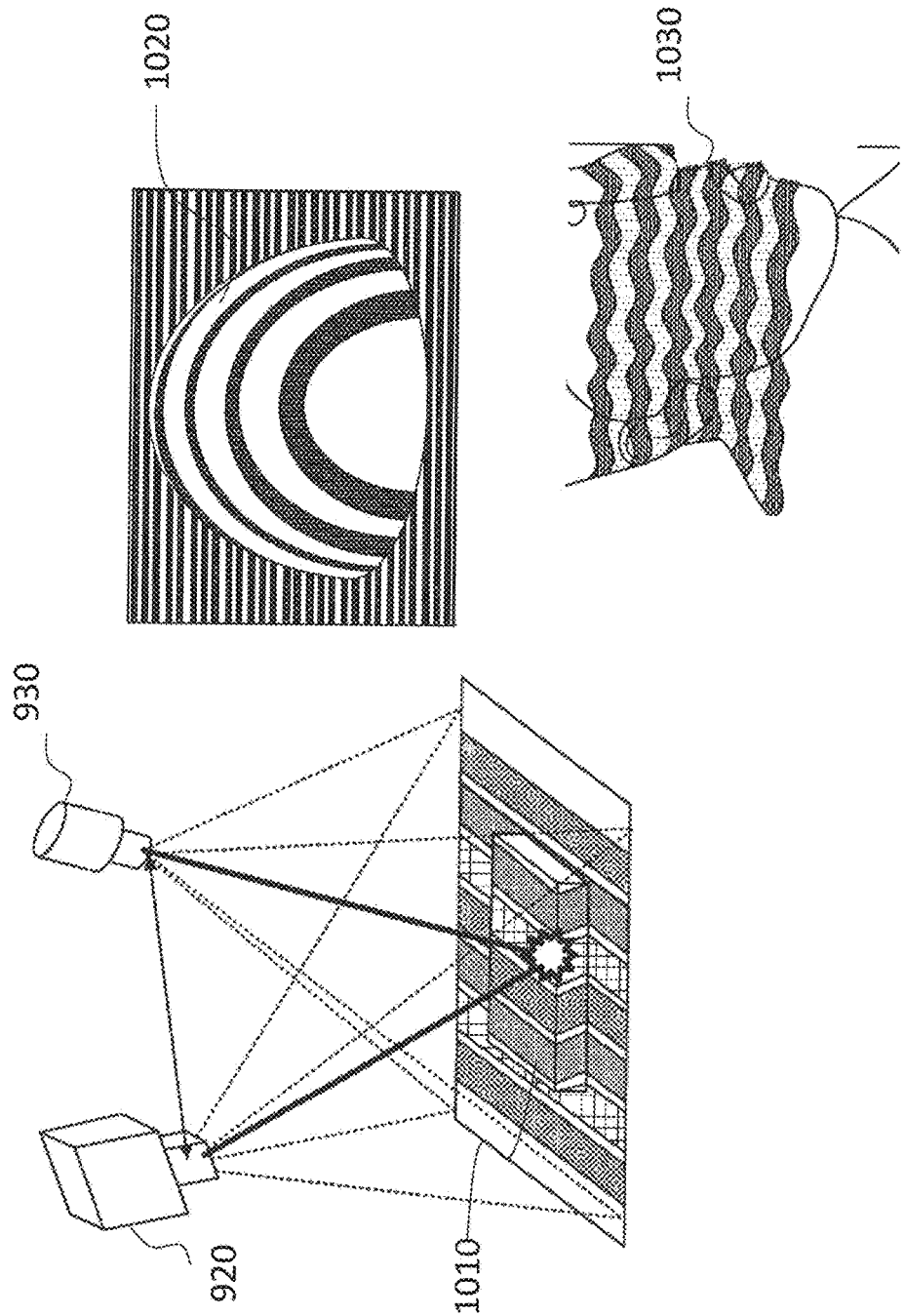
FIG. 10 is a diagram illustrating imaging a 3D object with a structured light source and camera, in accordance with some example embodiments.

FIG. 10 is a diagram illustrating imaging a 3D object 1010 with a structured light source 910 and camera 920, in accordance with some example embodiments. A camera 920 may image an object illuminated by structured light source 910. Geometric details of the illuminated object can be determined from the image as shown by the example of a hemisphere 1020. A structured light source may include illumination that is patterned or includes some form of spatial variations in intensity, wavelength, frequency, phase, or other properties of the light. By generating a predictable and predefined pattern of light on the surface to be scanned, the images of the pattern can be analyzed to determine distance or other surface features. For example, a structured light source may include a series of alternating light and dark bars, although other patterns may also be used. In some example embodiments, features of a three-dimensional object may be determined from the projection of the structured light onto the object. In one example, the projection onto the hemisphere 1020 of the alternating bars of light and dark causes the bars to appear wider due to the hemispherical shape when viewed from the side. FIG. 1030 also illustrates an example of an image showing a structured light pattern on the surface of a person. The structured light pattern generated inside the ear may be similar to the appearance of the structure light pattern on the person.

In some embodiments, the camera 920, or other detector, can detect structured light generated from a pattern imprinted on an interior surface of the inflatable membrane 110. For example, dots, lines, grids, or other visual patterns can be present on the inflatable membrane 110 prior to scanning. The pattern may be illuminated to generate structured light from the interior surface. In other embodiments, the emitter can emit structured light to form a pattern on the interior surface of the inflatable membrane 110 conforming to an interior shape of an ear and detecting the structured light generated by reflection from the interior surface. These may be done without using the medium 320 by, for example, inflating the inflatable membrane 110 with air or other uniformly attenuating material. Once the light is detected, the light can be analyzed as described herein to identify the shape of the scanned surface.

Figure 11:
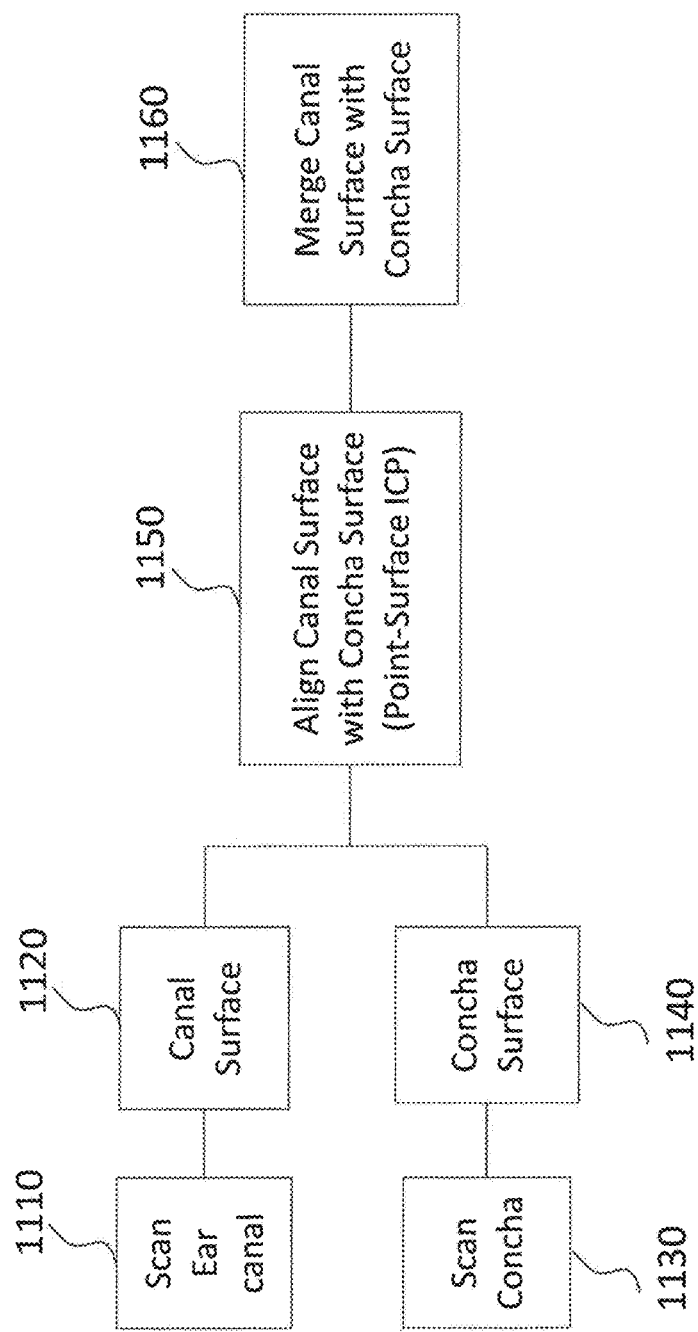
FIG. 11 is a process flow diagram illustrating combining a scan from a 3D scanner and another scan from a structured light source and camera, in accordance with some example embodiments.

FIG. 11 is a process flow diagram illustrating combining a scan from a 3D scanner 120 and another scan from a structured light source and camera, in accordance with some example embodiments. At 1110, a first scan of an ear may be taken using a 3D scanner 120 such as the scanner described in FIGS. 1-5. At 1120, the scan may be adjusted and/or processed to determine a shape of the ear canal. At 1130, another scan of the ear may be taken using a different type of scanner. For example, the structured light/camera assembly 940 may be used to generate a second scan. At 1140, the second scan may be adjusted and/or processed to determine a shape of the concha. In some example embodiments, the first scan and the second scan may be performed together at the same time. In some example embodiments, one scanner may perform both scans. For example, a 3D scanner 120 and a structured light source/camera assembly 940 may be combined into a single scanner. At 1150, the scan from the 3D scanner 120 and the scan from the structured light source/camera assembly 940 may be aligned with one another. For example, the position of first scan relative to the second scan may be adjusted so that a region of the ear captured by both scans may be used to align the two scans. After alignment, at 1160, the two scans may be merged.

In some example embodiments, the scans may be merged where the overlapping portions of the scans correspond to a transition region from one scan to the other scan. In some example embodiments, the scans in the transition region may be averaged with the scans being assigned equal weighting, or different weightings to preferentially bias the composite scan towards one scanning technique. For example, some methods described herein involve contact between the surface of the ear being scanned and any foreign object, such as the inflatable membrane 110. Because methods involving contact can cause mechanical deformation of the surface, this can introduce an error in measurement. When combining scans, methods that do not involve contact (such as membrane-less scans using a structured light source) may be biased to have greater weight than scans that did involve contact. The weighting may be on a pixel-by-pixel basis, such as based on a measurement or estimate of the amount of deformation of the ear surface, or can be constant over all pixels for the given scan type. The weighting may be applied to any interpolation/smoothing algorithms or be indicated graphically to a user manually merging the scans with modelling software.

In other embodiments, when the scans do not overlap, interpolation between the scans may be used to combine the scans. In another embodiment, one or more scans can be extrapolated to extend the effective scan surface. In other embodiments, the scans may be combined with input from an operator visually aligning the individual scans rendered on a computing device.

In other example embodiments, based on the electronic representation 200 or scans from either or both of the 3D scanner 120 and a structured light source/camera assembly 940, native references in the ear can be identified. Native references can be specific portions of the ear anatomy, for example, a concha, eardrum, or the like. Native references can also be specific contours of any portions of the ear anatomy. The native references may be referenced by the processor to facilitate combining scans by providing common points of reference. In some embodiments, this can be used with the structured light source/camera assembly 940 generating electronic representations of the ear where, due to the method not requiring the inflatable membrane 110, no deformation of the interior surface of the ear is performed.

Figure 12:
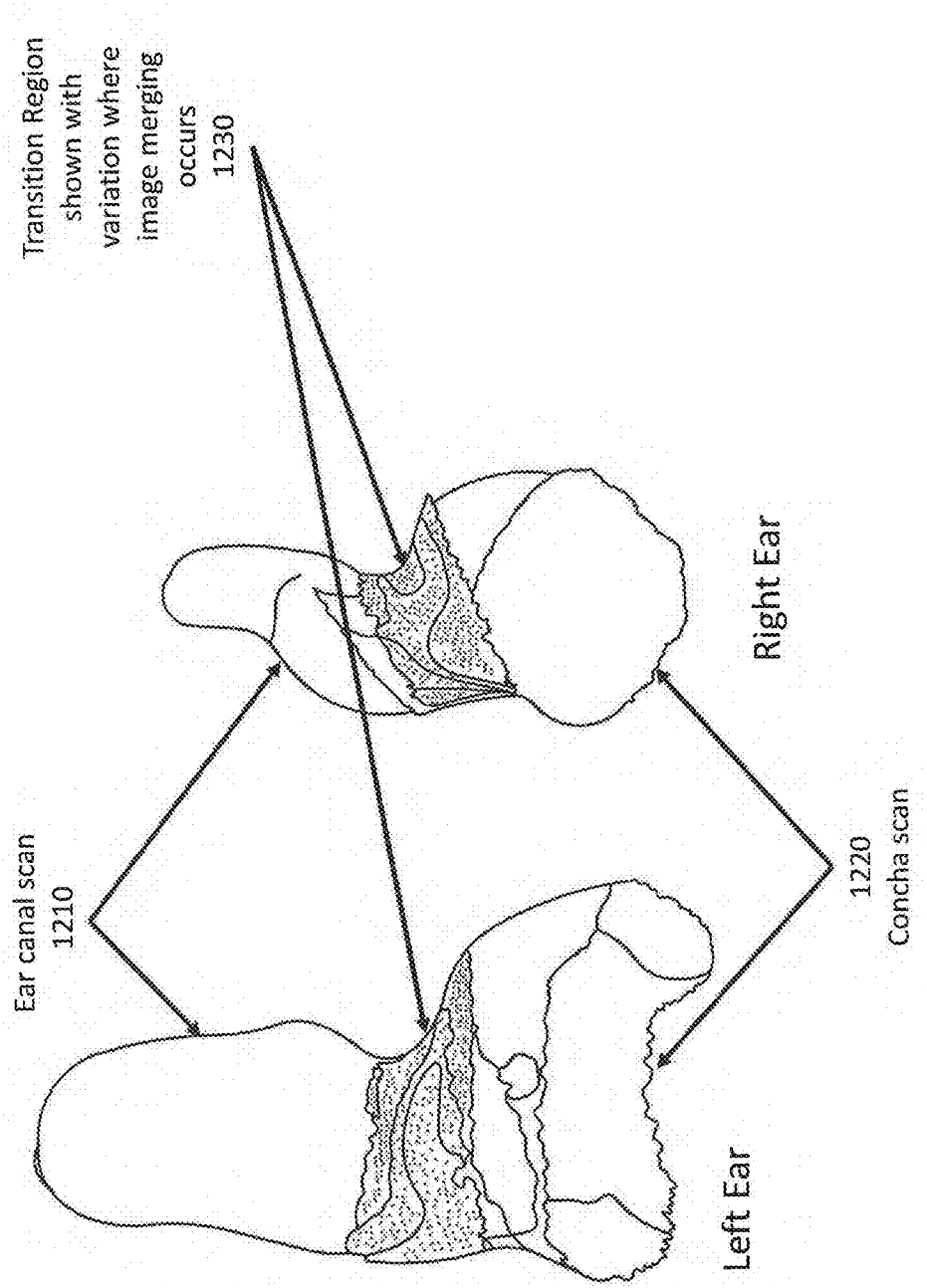
FIG. 12 is a diagram illustrating an example transition region between example scans from a 3D scanner and a structured light source and camera, in accordance with some example embodiments.

FIG. 12 is a diagram illustrating an example transition region between example scans from a 3D scanner 120 and a structured light source 930 and camera 920, in accordance with some example embodiments. Depicted at 1210 are example scans for the right and left ear canals from a conformal membrane scanner (also referred to herein as a 3D scanner 120) such as a scanner consistent with FIGS. 1-5. Depicted at 1220 are example scans for the right and left ears from another scanner such as a structured light source/camera assembly 940 disclosed in FIGS. 9-10. Depicted at 1230 are transition regions for the right and left ears. The transition regions may correspond to areas where the scan from the 3D scanner 120 and the scan using the structured light source 930 and camera 920 overlap. In some example embodiments, the transition regions 1230 may be determined using interpolation, or averaging, or other analytical method of merging the two scans. In some example embodiments, the transition regions 1230 may be adjusted by an operator. In regions where no scan was available, and interpolated, extrapolated, or otherwise synthetic data was used to merge actual scan surfaces, an indication of the transition region 1230 may be indicated with different colors, patterns, or other visual indicators.

In other implementations, a second scanner, or a second scan from the 3D scanner 120, may generate a second electronic representation of a second shape. The second shape may include a second interior shape of a portion of the cavity, a second portion of a second surface proximate to the cavity, or the like. The second interior shape can be another part of an ear or any other portion of the cavity 310. Similarly, the second portion of the second surface can be part of an area outside the cavity, such as the concha of an ear or other nearby external structural feature of the object being scanned. The second scanner can be, for example, the 3D scanner 120, a structured light source 910 and camera 920, or a laser rangefinder.

Figure 13:
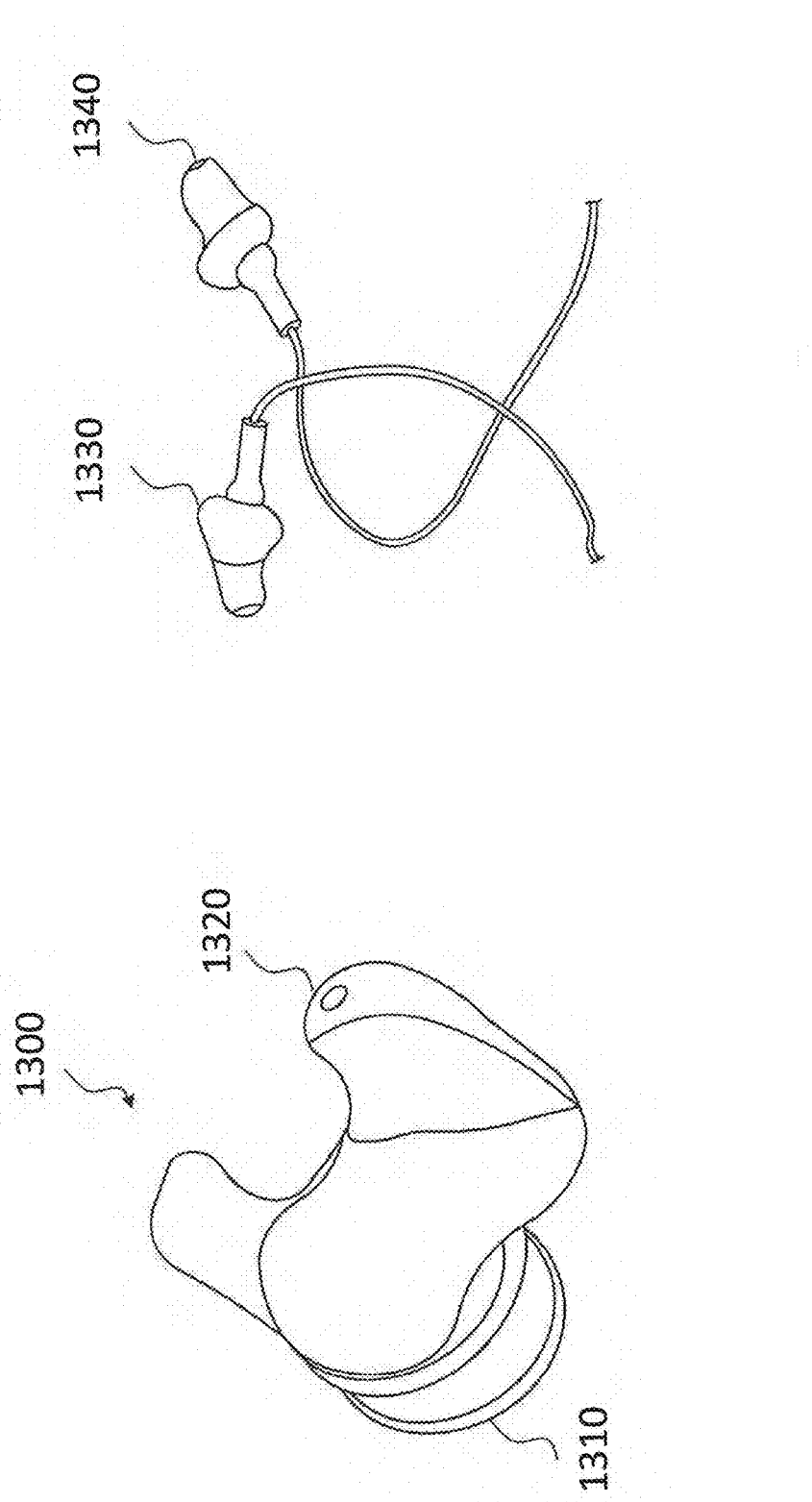
FIG. 13 is a diagram illustrating examples of earbud adapters, in accordance with some example embodiments.

FIG. 13 is a diagram illustrating examples of earbud adapters 1300, in accordance with some example embodiments. The earbud adapter 1300 may have an adapting portion 1310 to fit a commercial earbud or other earbud. Earbud adapter 1300 may have a customized portion 1320 custom-produced to fit a particular person's ear based on the scan. The customized portion 1320 may comprise a soft and/or flexible material. The adapting portion 1310 may comprise the same material or a different material. A right/left earbud adapter 1330 is shown coupled to a commercial earbud. A left/right earbud adapter 1340 is shown coupled to a commercial earbud is shown. The right and/or left earbuds may be colored so to distinguish the right and left earbuds/earbud adapters.

In accordance with some example embodiments, an earbud adapter 1300 may be made from a flexible material such as silicone. The earbud adapter 1300 may be produced from a scan performed on the ear canal to measure the size and shape of the ear canal. In some example embodiments, the scan may also determine the shape of the concha and/or other external ear shape. The earbud adapter 1300 may be made to fit the measured shape. The measured shape may be adjusted to reduce the length of the earbud in the ear canal, adjust the shape of the earbud on the surface outside the ear, and/or to change the shape to adapt the earbud to a standard earbud, or any other commercial earbud.

The fabrication process for earbuds or in-ear headphones may include adding speakers that may be wired devices or may be wireless devices. The additional components, for example, the speakers or wires, can be added by a second apparatus such as an automated manufacturing device. A wireless earbud may receive a signal transmitted from a cellular phone, music player or other electronic device. The sound generating devices may generate sound such as music or voice or may provide passive noise reduction and/or active noise cancellation. Passive noise reduction may occur due to the custom size and fit of the custom earbuds/earbud adapters and/or by a choice of the earbud material. For example, some earbud materials may provide more sound attenuation through the earbud than other materials. Active noise cancellation may include causing the sound generating devices in the earbuds to cancel noise that passes through or around the earbud at the ear canal side of the earbud. In this way, noise may be reduced at the ear canal. In some example embodiments, active noise cancellation may be performed in addition to sound generation of music or voice that the user has selected. For example, active noise cancellation and sound generation may be used to cancel aircraft noise and provide the user with music or voice during a flight.

Other additional components that may be included as part of the earbuds may include, for example, microphones, transmitters, receivers, padding, additional conformal adaptors to increase comfort or fit to the cavity 330, or the like. Also, the additional components can include biometric scanners, sensors, computer processors, electronic components for connected devices, or the like.

Figure 14:
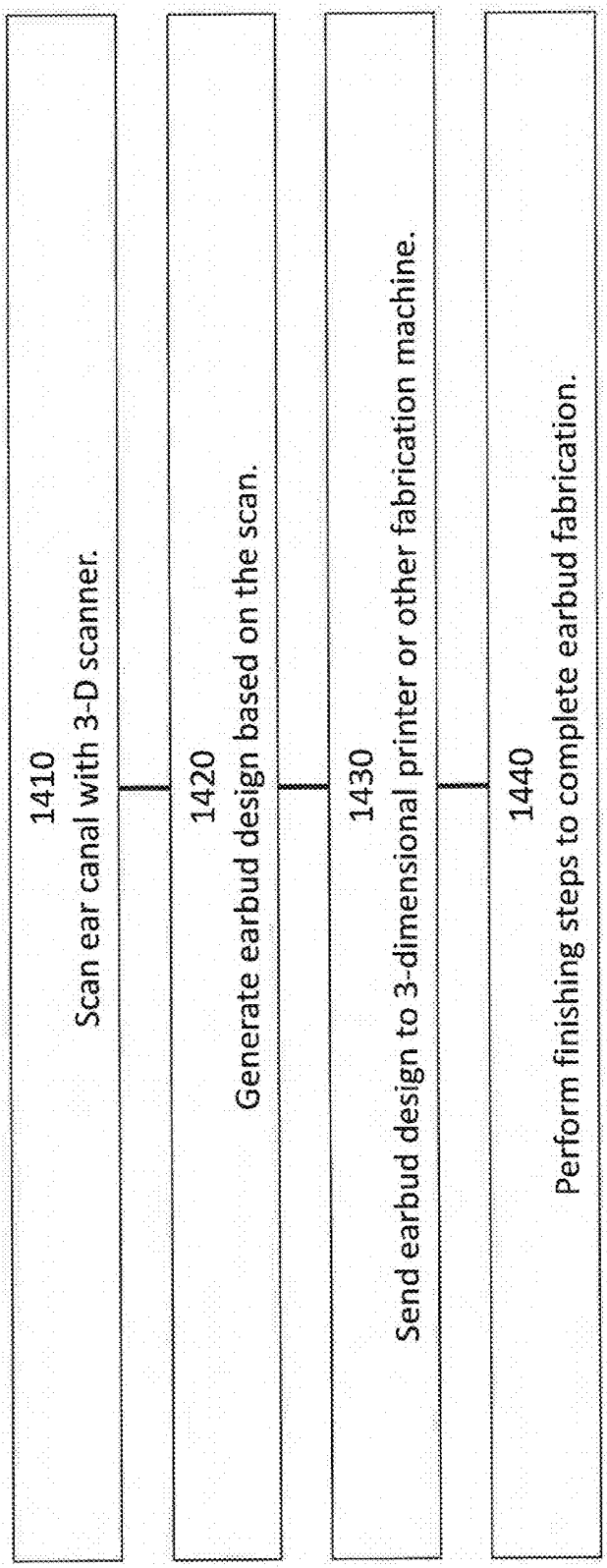
FIG. 14 is a process flow diagram illustrating a first process, in accordance with some example embodiments.

FIG. 14 is a process flow diagram illustrating a first process, in accordance with some example embodiments.

At 1410, the ear canal may be scanned by a scanner consistent with FIGS. 1-5. In some example embodiments, a second scanner consistent with FIGS. 9-10 may be used to scan the concha or other outer region of the ear. After the first ear is scanned, the second ear may be scanned. In some example embodiments, the shape of the ear canal and/or concha may be provided electronically as a 3D model or array of 2D models of the ear. In some example embodiments, the shape of the ear canal and/or concha may be determined from another source such as a magnetic resonance imaging or other imaging. In some example embodiments, the shape and/or model of the ear may be included in an electronic medical record.

At 1420, an earbud design may be produced based on the scan. In some example embodiments, the earbud design may include the scan after one or more adjustments. For example, the length of the earbud in the ear canal may be adjusted to be longer or shorter than the scanned ear canal. In some example embodiments, the length or external shape at the exterior of the ear may be adjusted. For example, the earbud may be adjusted in length to protrude more or less from the ear canal. In some example embodiments, the adjustments may include adjustments to cause improved attachment to the ear so that the earbud is less likely to fall out during use. In some example embodiments, the adjustments may include an opening at the exterior of the earbud to adapt and hold into place a standard earbud and/or other earbud.

At 1430, the earbud design may be produced on a fabrication machine. For example, the earbud design may be produced on a three-dimensional (3D) printer. In some example embodiments, a 3D printer may fabricate a 3D mechanical structure using one or more selectable materials. For example, a 3D printer may produce layers of material with selectable regions of the different materials. 3D printers may deposit regions of material that include polyamide, urethane, plastic, ceramic, metal, paper, wax, or other material. In some example embodiments, the earbud design may be produced on a 3D printer with the exterior regions of the earbud made using a shell of rigid material such as polyamide, urethane or other material and with the interior volume made from another material such as wax. The polyamide or urethane shell can be formed to a predetermined thickness, for example, between 0.05 mm and 2 mm. In some example embodiments, the removable material may have a lower melting point than the rigid material, or may be soluble in a solvent in which the rigid material is not soluble. The rigid exterior region may be referred to as an earbud shell. In some example embodiments, the wax from the interior of the earbud shell may be removed by heating the earbud shell and allowing the wax to drain out. For example, the wax may drain out when the shell is heated due to gravity or draining may be assisted by applying air pressure or placing the shell in a centrifuge. In some example embodiments, after the interior material such as wax has been removed, the earbud shell may be filled with a flexible material such as curable silicone or other material. After the silicone has cured in the shape of the interior of the earbud shell, the shell may be removed leaving the flexible earbud. The silicone or other flexible material may have a hardness of approximately 15-75 shore or other hardness. In some example embodiments, the earbud shells may be produced without a parting line for use one time. Earbud shells produced with a parting line may be used multiple times to make multiple earbuds. In some example embodiments, digital light processing (DLP) may be used instead of or in addition to 3D printing. In some example embodiments, DLP may include exposing light to liquid resin to produce a desired shape. In some example embodiments, DLP may result in solid objects without a shell and without the interior wax to remove.

At 1440, finishing steps may be performed on the flexible earbud. In some example embodiments, the earbud may be marked or color-coded so that earbuds may be easily identified and which earbud is for the right ear and which earbud is for the left ear. In some example embodiments, the earbud may be smoothed, marked, rinsed, cleaned, and/or prepared for use.

Figure 15:
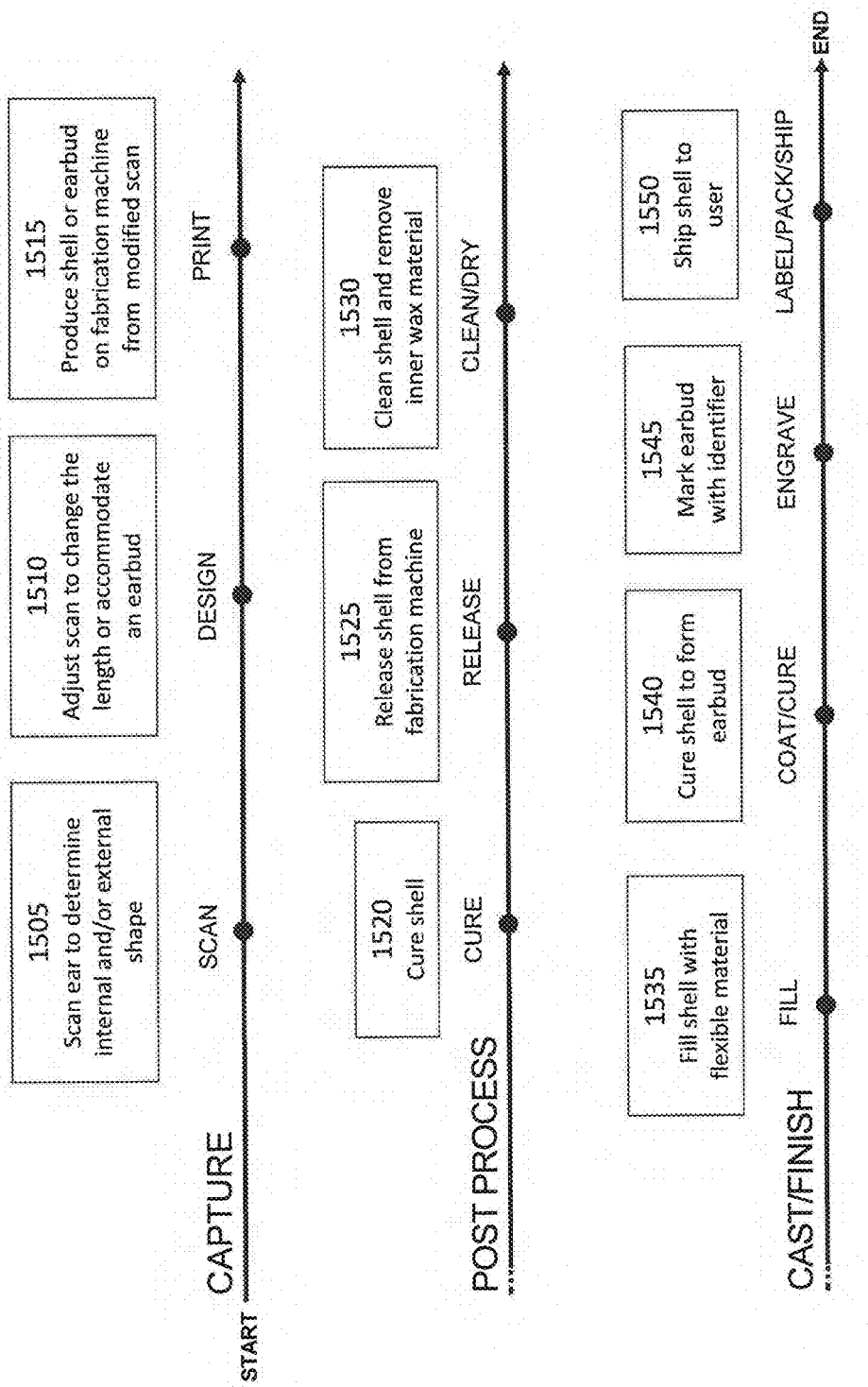
FIG. 15 is a process flow diagram illustrating a second process, in accordance with some example embodiments.

FIG. 15 is a process flow diagram illustrating a second process, in accordance with some example embodiments.

At 1505, an ear may be scanned to determine the internal and/or external shape of the scanned ear. In some example embodiments, the scanning may be performed using an optical scanner such as the scanner described with respect to FIGS. 1-5. In some example embodiments, the scan may be performed using a different type of scanner such as a photographic scanner, magnetic resonance imaging, dye enhanced, or other scanner. In some example embodiments, the shape of the ear may be provided electronically as a 3D model or an array of 2D models or images. The shape/model may be part of an electronic medical record.

At 1510, the scan may be adjusted to change the length and/or accommodate an earbud. In some example embodiments, the earbud design may include the scan after one or more adjustments. In some example embodiments, the scan, or a mathematical or electronic model of the scan, may be adjusted using a design computer that may run 3D design/ modelling software, Computer-Aided Drafting/Drawing (CAD) software, or the like. The design computer can be configured to modify one or more electronic representations into a three-dimensional shape corresponding to at least a portion of the interior shape of the ear. For example, the length of the earbud in the ear canal may be adjusted to be shorter than the scanned ear canal. In some example embodiments, the length or external shape of the earbud at the exterior of the ear may be adjusted. For example, the earbud may be adjusted in length to protrude more or less from the ear canal. In some example embodiments, the adjustments may include adjustments to cause improved attachment to the ear so that the earbud is less likely to fall out during use. In some example embodiments, the adjustments may include an opening at the exterior of the earbud to adapt and hold into place a standard earbud and/or other earbud.

At 1515, a shell or earbud may be produced on a fabrication machine from the modified electronic representation or scan. In some example embodiments, a 3D printer or digital light processing system may be used to produce earbud shells. For example, a 3D printer may "print" or deposit successive layers of material to produce a 3D object. For example, a 3D printer may deposit two materials in successive layers such as a hard or rigid material on outside surfaces to produce a shell, and another material that is removable in the interior such as wax that aids in supporting the shell as the layers are deposited. In some example embodiments, the removable material may have a lower melting point than the rigid material, or may be soluble in a solvent in which the rigid material is not soluble. The 3D printer may be controlled by a computer to produce earbud shells in accordance with the scanned ear or the adjusted scan of the ear. In some example embodiments, extrusion and sintering-based processes may be used. The 3D printed shells may be produced by the 3D printer on a plate. The shells may then be cleaned or rinsed.

At 1520, the shell may be cured. For example, the shell may be cured over a time period with or without being heated in an oven.

At 1525, the shell may be released. For example, the earbuds may be released from a plate associated with the 3D printer.

At 1530, the shell may be cleaned and the inner wax material may be melted and drained out of the shells. For example, the wax in the shells may be melted in the oven at a temperature such as 70 degrees Celsius or another temperature for 45 minutes or another amount of time. The earbud shells with the internal wax removed may be cleaned using a solution such as mineral oil, at a particular temperature for a particular amount of time. For example, the earbud shells may be cleaned with mineral oil at 70 degrees Celsius for 15 minutes. The shells may be further cleaned and/or rinsed with a second liquid such as water. The shells may be dried using compressed air and/or placing the shells in an oven at, for example, 70 degrees Celsius.

At 1535, the shell may be filled with a flexible material. For example, the earbud shells may be filled by injecting silicone or another flexible material into the shells. The injected compound may be liquid before curing and solid after curing.

At 1540, the material in the shell may be cured to form the earbud. In some example embodiments, the material in the shell may include silicone. Pressure may be applied to the filled earbud shells by, for example, a pressure pot. For example, the pressure pot may be held at a pressure of 6 bars at a temperature of 85 degrees Celsius for 10 minutes. After the material such as silicone in the shells has cured, the shells may be removed. In some example embodiments, shells made without a parting line may be removed by cracking them with an arbor press. In some example embodiments, shells made with a parting line may not require cracking. In some example embodiments, a shell post may be removed in a central portion of the earbud. In some example embodiments, a grinder may be used to finish the earbud to ensure smoothness and remove any excess material remaining from the silicone injection process. In some example embodiments, the left and right earbuds may be marked in order to tell them apart. For example, the right and left earbuds may be marked with dyed silicone. For example, a small hole may be made in each earbud and colored silicone added. Additional curing, cleaning, rinsing, and drying may be performed. In some example embodiments, the earbuds may be lacquered. A centrifuge may be used to ensure the lacquer coating is thin. For example, the lacquered earbuds may be placed in a centrifuge at 500 RPM a few seconds. In some example embodiments, the lacquered earbuds may be dried under pressure at 85 degrees Celsius for 5 minutes.

At 1545, the earbud may be marked with an identifier. For example, each earbud may be marked with an identifier to ensure that the correct earbud is sent to a user. The right and left earbuds may be marked using different colors so that the user can visually distinguish the right earbud from the left earbud.

At 1550, the earbud may be shipped to a user.

Though the methods, apparatus, and systems are described herein with respect to an earpiece and scanning an ear canal, these methods, apparatus, and systems may be applied to any cavity 330 or orifice assembly for scanning any suitable anatomical cavity 330. For example, the methods, apparatus, and systems can be used for scanning oral, nasal, renal, intestinal, or other anatomical cavities, and can involve assemblies designed for those anatomical cavities. Further, these methods, apparatus, and systems may be used with sensitive or fragile cavities that are not anatomical in nature, such as those made from brittle, pliable, or otherwise delicate materials.

Without in any way limiting the scope, interpretation, or application of the claims appearing below, a technical effect of one or more of the example embodiments disclosed herein is reusability of certain components. Moreover, without in any way limiting the scope, interpretation, or application of the claims appearing below, a technical effect of one or more of the example embodiments disclosed herein is that the medium providing assembly may be used for multiple scans, including for multiple patients. In some implementations, the absorbing medium and medium providing assembly may be used for 10-15 scans or more. Furthermore, without in any way limiting the scope, interpretation, or application of the claims appearing below, a technical effect of one or more of the example embodiments disclosed herein is that the absorbing medium, and the system as a whole, may be more likely to be shelf-stable, as it can be shipped without contacting the inflatable membrane until just before scanning.

Figure 16:
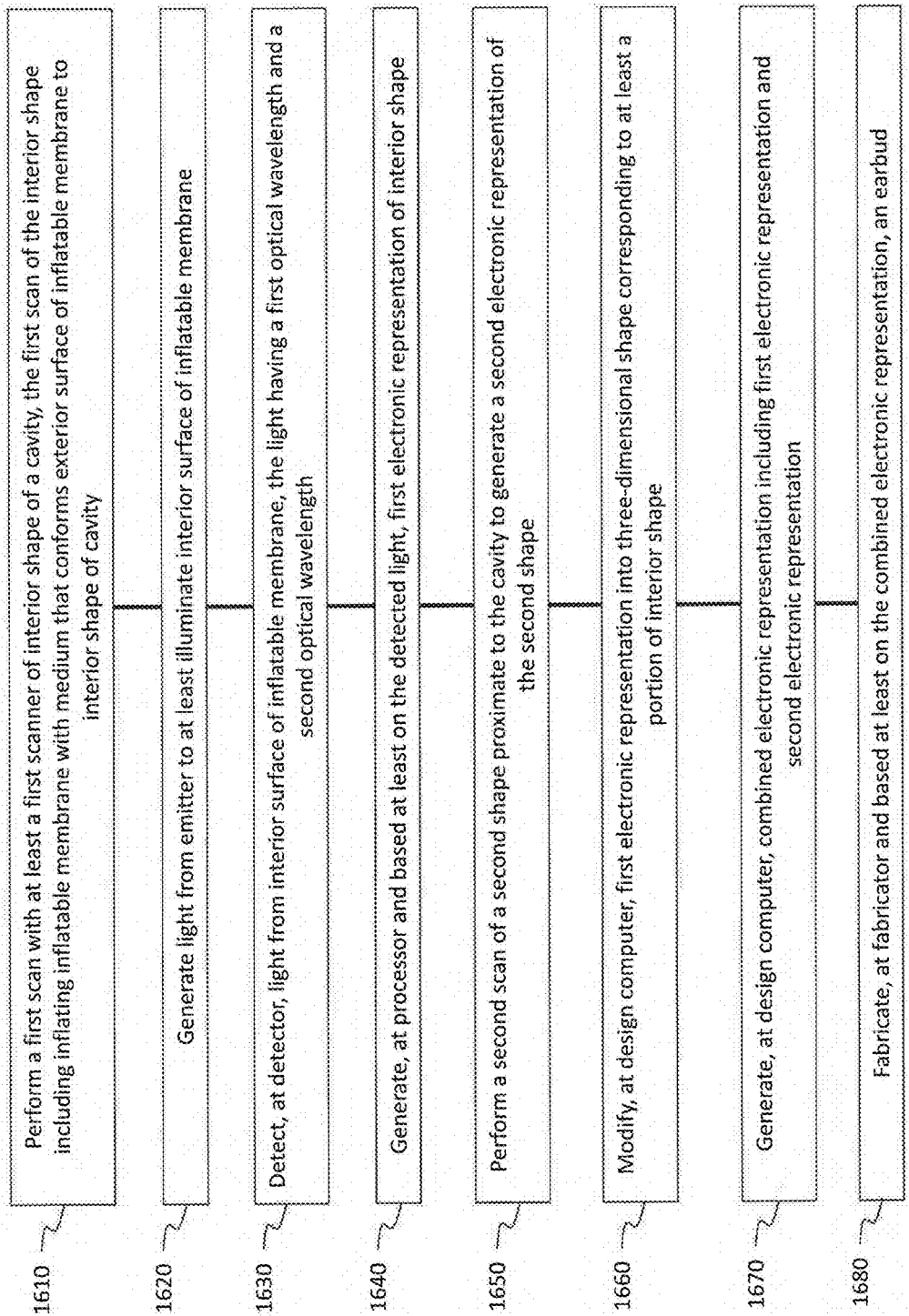
FIG. 16 is a process flow diagram illustrating a third process, in accordance with some example embodiments.

FIG. 16 is a process flow diagram illustrating a third process, in accordance with some example embodiments.

At 1610, the 3D scanner 120 may scan an interior shape of a cavity 330. The scanning may include inflating an inflatable membrane with a medium 310 to conform an exterior surface of the inflatable membrane 110 to an interior shape of a cavity 330. For example, the 3D scanner 120 can be coupled to the inflatable membrane 110 as shown in FIG. 1.

At 1620, light can be generated from an emitter to illuminate the interior surface of the inflatable membrane 110. For example, the light may illuminate fluorescent portions of the inflatable membrane 110, illuminate a pattern imprinted on the inflatable membrane 110, create a structured light pattern on the inside of the inflatable membrane 110, or the like.

At 1630, a detector may detect light emitted from the interior surface of the inflatable membrane 110. For example, the light may include a first optical wavelength and a second optical wavelength. The first optical wavelength and the second optical wavelength may be generated by differential attenuation of fluorescing light from the inflatable membrane, reflection of light from the inflatable membrane where the light was first generated by a multiple-wavelength emitter, reflection of light from a pattern on the inflatable membrane, or the like.

At 1640, a processor may generate a first electronic representation 200 of the interior shape based at least on the detected light. For example, the first electronic representation 200 may be a 3D rendering generated by computer software and processor that combines one or more surfaces imaged by the 3D scanner 120. The first electronic representation 200 may be combined by interpolating or otherwise digitally expanding/merging image portions, acquired by the 3D scanner 120 or other scanning technique, into a composite image of the ear.

At 1650, a second shape proximate to the cavity 330 may be scanned to generate a second electronic representation of the second shape. For example, the second shape may correspond to an outer part of the object scanned, or be another scan that overlaps some or all of the interior shape scanned with the 3D scanner or other scanning device.

At 1660, the design computer may modify the first electronic representation into a three-dimensional shape corresponding to at least a portion of the interior shape. For example, the modification may include digital deformation of the first electronic representation, rotation, translation, or other adjustment performed in software automatically or by a user.

At 1670, the design computer may generate a combined electronic representation from the first electronic representation and the second electronic representation. For example, the combined electronic representation may include interpolating, extrapolating, or otherwise connecting features of the first electronic representation and the second electronic representation.

At 1680, the fabricator may fabricate an earbud according to the combined electronic representation. The fabrication process may include translating the combined electronic representation to instructions that for operation of a 3D printer or other fabrication machine. The fabrication process can also include forming a mold based on the combined electronic representation.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed:

1. A system comprising:
    a first scanner comprising:
        an inflatable membrane configured to be inflated with a medium to conform an exterior surface of the inflatable membrane to an interior shape of a cavity, the medium attenuating, at first rate per unit length, light having a first optical wavelength, and attenuating, at a second rate per unit length, light having a second optical wavelength;
        an emitter configured to generate light to illuminate an interior surface of the inflatable membrane;
        a detector configured to receive light from the interior surface of the inflatable membrane, the received light comprising light at the first optical wavelength and the second optical wavelength; and
        a processor configured to generate a first electronic representation of the interior shape based on the received light;
    a design computer configured to modify the first electronic representation into a three-dimensional shape corresponding to at least a portion of the interior shape; and
    a fabricator configured to fabricate, based at least on the modified first electronic representation, an earbud, wherein the first scanner comprises a scanning tip, wherein the scanning tip comprises the emitter and the detector, and wherein the scanning tip is configured to actuate between an extended position and a retracted position.

2. The system of claim 1, further comprising: a second scanner comprising a structured light source and a camera, the second scanner configured to generate a second electronic representation of a second shape, the second shape being of at least one of: a second interior shape of a portion of the cavity; and a second portion of a second surface proximate to the cavity.

3. The system of claim 2, wherein the design computer is further configured to merge the first electronic representation and the second electronic representation into a combined electronic representation of the interior shape and the second shape.

4. The system of claim 2, wherein the second scanner is coupled to the first scanner.

5. The system of claim 1, wherein the fabricator comprises at least one of: a mold for the earbud, the mold based at least on the interior shape; a three-dimensional printer or digital light processing system; and a second apparatus configured to add one or more additional components to the earbud, the one or more additional components comprising at least one component for delivering sound to an area proximal to the earbud.

6. The system of claim 5, wherein the three-dimensional printer is configured to fabricate an object comprising a shell with a predetermined thickness, and wherein the shell corresponds to the interior shape.

7. A method comprising:
    performing a first scan, with at least a first scanner, of an interior shape of a cavity, the first scan of the interior shape comprising:
        inflating an inflatable membrane with a medium, the inflating of the inflatable membrane conforms an exterior surface of the inflatable membrane to the interior shape of the cavity;
        generating light from an emitter to at least illuminate an interior surface of the inflatable membrane;
        detecting, at a detector, light from the interior surface of the inflatable membrane, the light comprising a first optical wavelength and a second optical wavelength; and
        generating, at a processor, a first electronic representation of the interior shape, the generating being based at least on the detected light;
    performing a second scan of a second shape proximate to the cavity, the second scan of the second shape generates a second electronic representation of the second shape;
    modifying, at a design computer, the first electronic representation into a three-dimensional shape corresponding to at least a portion of the interior shape;
    generating, at the design computer, a combined electronic representation comprising the first electronic representation and the second electronic representation;
    fabricating, at a fabricator, an earbud, the fabricating based at least on the combined electronic representation; and
    actuating, between an extended position and a retracted position, a scanning tip, the scanning tip comprising the emitter and the detector and the scanning tip being actuated during the generating and detecting of the light.

8. The method of claim 7, wherein the second scan is performed by a second scanner, wherein the second scanner comprises at least one of the first scanner, a structured light source and a camera, and a laser rangefinder.

9. The method of claim 7, further comprising: illuminating a surface with a structured light source, the structured light source emitting light having spatial variations of intensity or wavelength; imaging the illuminated interior surface with a camera, wherein the imaging generates one or more images resulting from the light having spatial variations; and generating, based at least on the one or more images, the second electronic representation of the surface.

10. The method of claim 7, wherein the first electronic representation is generated based at least on measurements of absorption of the light at the first optical wavelength and measurements of absorption of the light at the second optical wavelength.

11. The method of claim 7, further comprising: identifying, based at least on the second electronic representation, one or more native references within the interior shape and the second shape; and combining, based at least on the one or more native references, a plurality of electronic representations.

12. The method of claim 7, wherein the fabricating comprises at least one of:
forming, based at least on the interior shape, a mold for the earbud; fabricating the earbud with a three-dimensional printer or a digital light processing system; and adding, with a second apparatus, one or more additional components to the earbud, one or more the additional components comprising at least one component for delivering sound to an area proximal to the earbud.

13. A method comprising:
performing a first scan, with at least a first scanner, of an interior shape of a cavity, the first scan of the interior shape comprising detecting, at a detector, light comprising a first optical wavelength and a second optical wavelength, the detected light generated by at least one of:
detecting structured light generated from a pattern imprinted on an interior surface of an inflatable membrane; and
emitting, by an emitter, structured light to form a pattern on the interior surface of the inflatable membrane conforming to an interior shape of an ear and the detected light generated by reflection of the structured light from the interior surface; and
generating, at a processor, a first electronic representation of the interior shape, the generating being based at least on the detected structured light;
performing a second scan of a second shape proximate to the cavity, the second scan of the second shape generates a second electronic representation of the second shape;
modifying, at a design computer, the first electronic representation into a three-dimensional shape corresponding to at least a portion of the interior surface;
generating, at the design computer, a combined electronic representation comprising the first electronic representation and the second electronic representation;
fabricating, at a fabricator, an earbud, the fabricating based at least on the combined electronic representation; and
actuating, between an extended position and a retracted position, a scanning tip, the scanning tip comprising the emitter and the detector and the scanning tip being actuated during the generating and the detecting of the light.

14. The method of claim 13, wherein the second scan is performed by a second scanner, wherein the second scanner comprises at least one of the first scanner, a structured light source and a camera, and a laser rangefinder.

15. The method of claim 13, further comprising: illuminating a surface with a structured light source, the structured light source emitting light having spatial variations of intensity or wavelength; imaging the illuminated interior surface with a camera, the imaging generates one or more images resulting from the light having spatial variations; and generating, based at least on the one or more images, the second electronic representation of the surface.

16. The method of claim 13, wherein the first electronic representation is generated based at least on measurements of absorption of the light at the first optical wavelength and measurements of absorption of the light at the second optical wavelength.

17. The method of claim 13, further comprising: identifying, based at least on the second electronic representation, one or more native references within the interior shape and the second shape; and combining, based at least on the one or more native references, a plurality of electronic representations.

18. The method of claim 13, wherein the fabricating comprises at least one of:
forming, based at least on the interior shape, a mold for the earbud; fabricating the earbud with a three-dimensional printer or a digital light processing system; and adding, with a second apparatus, one or more additional components to the earbud, one or more the additional components comprising at least one component for delivering sound to an area proximal to the earbud.

* * * * *

UNITED STATES PATENT AND TRADEMARK OFFICE
CERTIFICATE OF CORRECTION

PATENT NO. : 10,122,989 B2  
APPLICATION NO. : 15/289061  
DATED : November 6, 2018  
INVENTOR(S) : Robert J. Fei et al.

Page 1 of 1

It is certified that error appears in the above-identified patent and that said Letters Patent is hereby corrected as shown below:

In the Specification

In Column 6, Line 59, delete "and or" and insert -- and/or --, therefor.

In Column 8, Line 6, delete "$I_1(x)=I_1(0)e^{-\mu 1x}$," and insert -- $I_1(x) = I_1(0)e^{-\mu_1 x}$ --, therefor.

In Column 8, Line 11, delete "$I_2(x)=I_2(0)e^{-\mu 2x}$," and insert -- $I_2(x) = I_2(0)e^{-\mu_2 x}$ --, therefor.

In Column 9, Line 26, delete "the a" and insert -- a --, therefor.

Signed and Sealed this  
Second Day of April, 2019

Andrei Iancu  
*Director of the United States Patent and Trademark Office*